United States Patent
Miesel et al.

(10) Patent No.: US 11,426,514 B2
(45) Date of Patent: Aug. 30, 2022

(54) IMPLANTABLE MEDICAL PUMP WITH PRESSURE SENSOR

(71) Applicant: Medtronic, Inc., Minneapolis, MN (US)

(72) Inventors: Keith A. Miesel, St. Paul, MN (US); James M. Haase, Maplewood, MN (US); Chris J. Paidosh, Minneapolis, MN (US); Darren A. Janzig, Center City, MN (US); Timothy J. Denison, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 371 days.

(21) Appl. No.: 16/565,013

(22) Filed: Sep. 9, 2019

(65) Prior Publication Data

US 2020/0001007 A1  Jan. 2, 2020

Related U.S. Application Data

(63) Continuation of application No. 15/681,957, filed on Aug. 21, 2017, now Pat. No. 10,406,281, which is a
(Continued)

(51) Int. Cl.
*A61M 5/142* (2006.01)
*A61M 39/02* (2006.01)
(Continued)

(52) U.S. Cl.
CPC .... *A61M 5/14276* (2013.01); *A61M 39/0208* (2013.01); *G01L 9/0072* (2013.01);
(Continued)

(58) Field of Classification Search
CPC .. A61M 2205/3317; A61M 2205/3331; A61M 39/0208; A61M 5/14276;
(Continued)

(56) References Cited

U.S. PATENT DOCUMENTS 4,443,218 A   4/1984 DeCant et al.
5,150,275 A   9/1992 Lee et al.
(Continued)

FOREIGN PATENT DOCUMENTS

WO   9528623 A1   10/1995
WO   0072747 A1   12/2000

OTHER PUBLICATIONS

International Preliminary Report on Patentability from International Application No. PCT/US2011/034068, dated Dec. 4, 2012, 9 pp.
(Continued)

*Primary Examiner* — Quynh-Nhu H. Vu
(74) *Attorney, Agent, or Firm* — Shumaker & Sieffert, P.A.

(57) ABSTRACT

The disclosure is directed to a pressure sensor of an implantable medical device. The pressure sensor may utilize detect fluid pressure based on a changing capacitance between two capacitive elements. The pressure sensor may define at least a portion of a fluid enclosure of the IMD. In one example, the pressure sensor has a self-aligning housing shape that occludes an opening in the pump bulkhead of the IMD. An operative surface of the pressure and the portion of the fluid enclosure may be formed of a corrosion resistant and/or biocompatible material. A first capacitive element of the pressure sensor may be a metal alloy diaphragm that deflects in response to external fluid pressure. A second capacitive element of the pressure sensor may be a metal coating on a rigid insulator sealed from the fluid by the diaphragm and a housing of the sensor.

27 Claims, 18 Drawing Sheets

Related U.S. Application Data continuation of application No. 12/793,457, filed on Jun. 3, 2010, now Pat. No. 9,737,657.

(51) Int. Cl.
| | |
|---|---|
| *G01L 9/00* | (2006.01) |
| *G01L 15/00* | (2006.01) |
| *G01L 19/00* | (2006.01) |
| *G01L 19/08* | (2006.01) |
| *G01L 19/14* | (2006.01) |

(52) U.S. Cl.
CPC .......... *G01L 15/00* (2013.01); *G01L 19/0023* (2013.01); *G01L 19/0069* (2013.01); *G01L 19/086* (2013.01); *G01L 19/143* (2013.01); *G01L 19/148* (2013.01); *G01L 19/149* (2013.01); *A61M 2205/3317* (2013.01); *A61M 2205/3331* (2013.01)

(58) Field of Classification Search
CPC . G01L 15/00; G01L 19/0023; G01L 19/0069; G01L 19/086; G01L 19/143; G01L 19/148; G01L 19/149; G01L 9/0072
See application file for complete search history.

(56) References Cited

U.S. PATENT DOCUMENTS

| | | | |
|---|---|---|---|
| 5,157,972 A | 10/1992 | Broden | |
| 5,264,075 A | 11/1993 | Zanini-Fisher et al. | |
| 5,315,877 A | 5/1994 | Park et al. | |
| 5,328,460 A | 7/1994 | Lord et al. | |
| 5,488,869 A | 2/1996 | Renaud | |
| 5,507,737 A * | 4/1996 | Palmskog .......... A61M 5/14276 | |
| | | | 604/288.02 |
| 5,564,434 A | 10/1996 | Halperin et al. | |
| 5,709,337 A | 1/1998 | Moser et al. | |
| 5,880,372 A | 3/1999 | Nasiri | |
| 5,939,640 A | 8/1999 | Hauser | |
| 6,106,477 A | 8/2000 | Miescl et al. | |
| 6,171,252 B1 | 1/2001 | Roberts | |
| 6,349,740 B1 | 2/2002 | Cho et al. | |
| 6,423,029 B1 | 7/2002 | Elsberry | |
| 6,485,465 B2 | 11/2002 | Moberg et al. | |
| 6,532,834 B1 | 3/2003 | Pinto et al. | |
| 6,589,205 B1 | 7/2003 | Meadows | |
| 6,620,151 B2 | 9/2003 | Blischak et al. | |
| 6,659,980 B2 | 12/2003 | Moberg et al. | |
| 6,666,826 B2 | 12/2003 | Salo et al. | |
| 6,764,446 B2 | 7/2004 | Wolinsky et al. | |
| 6,789,429 B2 | 9/2004 | Pinto et al. | |
| 6,829,507 B1 | 12/2004 | Lidman et al. | |
| 6,830,558 B2 | 12/2004 | Flaherty et al. | |
| 6,968,743 B2 | 11/2005 | Rich et al. | |
| 6,969,369 B2 | 11/2005 | Struble | |
| 6,976,982 B2 | 12/2005 | Santini, Jr. et al. | |
| 7,149,587 B2 | 12/2006 | Wardle et al. | |
| 7,155,284 B1 | 12/2006 | Whitehurst et al. | |
| 7,236,821 B2 | 6/2007 | Cates et al. | |
| RE39,863 E | 10/2007 | Smith | |
| 7,320,676 B2 | 1/2008 | Miesel | |
| 7,338,464 B2 | 3/2008 | Blischak et al. | |
| 7,347,826 B1 | 3/2008 | Karicherla et al. | |
| 7,360,428 B2 | 4/2008 | Banholzer et al. | |
| 7,367,968 B2 | 5/2008 | Rosenberg et al. | |
| 7,390,311 B2 | 6/2008 | Hildebrand et al. | |
| 7,491,181 B2 | 2/2009 | Heruth et al. | |
| 7,505,869 B2 | 3/2009 | Hartlaub | |
| 7,590,449 B2 | 9/2009 | Mann et al. | |
| 7,591,185 B1 | 9/2009 | Mothilal et al. | |
| 7,616,991 B2 | 11/2009 | Mann et al. | |
| 7,621,905 B2 | 11/2009 | Penner et al. | |
| 7,637,892 B2 | 12/2009 | Steinbach et al. | |
| 7,650,191 B1 | 1/2010 | Lim et al. | |
| 7,677,107 B2 | 3/2010 | Nunez et al. | |
| 7,717,854 B2 | 5/2010 | Mann et al. | |
| 7,744,560 B2 | 6/2010 | Struble | |
| 7,744,618 B2 | 6/2010 | Shuros et al. | |
| 7,765,875 B2 | 8/2010 | Guo | |
| 7,850,676 B2 | 12/2010 | Wood, Jr. | |
| 7,862,513 B2 | 1/2011 | Eigler et al. | |
| 7,867,192 B2 | 1/2011 | Bowman et al. | |
| 7,875,004 B2 | 1/2011 | Y odfat et al. | |
| 7,900,518 B2 | 3/2011 | Tai et al. | |
| RE42,378 E | 5/2011 | Wolinsky et al. | |
| 8,012,120 B2 | 9/2011 | Slate et al. | |
| 8,397,578 B2 | 3/2013 | Miesel et al. | |
| 9,737,657 B2 | 8/2017 | Miesel et al. | |
| 10,406,281 B2 | 9/2019 | Miesel et al. | |
| 2002/0040208 A1 | 4/2002 | Flaherty et al. | |
| 2002/0087146 A1 | 7/2002 | Schu et al. | |
| 2003/0036746 A1 | 2/2003 | Penner et al. | |
| 2004/0035211 A1 | 2/2004 | Pinto et al. | |
| 2004/0102806 A1 | 5/2004 | Broome et al. | |
| 2004/0133166 A1 | 7/2004 | Moberg et al. | |
| 2004/0204673 A1 | 10/2004 | Flaherty | |
| 2005/0038371 A1 | 2/2005 | Reich et al. | |
| 2005/0165456 A1 | 7/2005 | Mann et al. | |
| 2005/0208095 A1 | 9/2005 | Hunter et al. | |
| 2005/0234393 A1 | 10/2005 | Wood, Jr. | |
| 2005/0234399 A1 | 10/2005 | Wood, Jr. | |
| 2005/0234431 A1 | 10/2005 | Williams et al. | |
| 2005/0249606 A1 | 11/2005 | Rush | |
| 2005/0288596 A1 | 12/2005 | Eigler et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0089619 A1* | 4/2006 | Ginggen .......... A61M 5/14276 | |
| | | | 604/288.02 |
| 2006/0149324 A1 | 7/2006 | Mann et al. | |
| 2006/0149330 A1 | 7/2006 | Mann et al. | |
| 2006/0276744 A1 | 12/2006 | Falk | |
| 2007/0021680 A1 | 1/2007 | Mills | |
| 2007/0083153 A1 | 4/2007 | Haar | |
| 2007/0168150 A1 | 7/2007 | Hirata et al. | |
| 2007/0199385 A1 | 8/2007 | O'Brien et al. | |
| 2007/0233019 A1 | 10/2007 | Forsell | |
| 2007/0261496 A1* | 11/2007 | Jonsson .............. A61M 1/3639 | |
| | | | 73/723 |
| 2008/0000531 A1 | 1/2008 | Robb et al. | |
| 2008/0177350 A1 | 7/2008 | Kieval et al. | |
| 2008/0243016 A1 | 10/2008 | Liao et al. | |
| 2008/0243093 A1 | 10/2008 | Kalpin et al. | |
| 2008/0300659 A1 | 12/2008 | Matos | |
| 2008/0306466 A1 | 12/2008 | Shelton et al. | |
| 2009/0082757 A1 | 3/2009 | Rogers et al. | |
| 2009/0112103 A1 | 4/2009 | Kassem | |
| 2009/0118667 A1 | 5/2009 | Haueter et al. | |
| 2009/0149810 A1 | 6/2009 | Ring et al. | |
| 2009/0158853 A1 | 6/2009 | Berner et al. | |
| 2009/0270844 A1 | 10/2009 | Seeley et al. | |
| 2010/0016918 A1 | 1/2010 | Mann et al. | |
| 2010/0022992 A1 | 1/2010 | Genosar et al. | |
| 2010/0030293 A1 | 2/2010 | Sarkar et al. | |
| 2010/0076398 A1 | 3/2010 | Scheurer et al. | |
| 2010/0100079 A1 | 4/2010 | Berkcan et al. | |
| 2010/0106082 A1 | 4/2010 | Zhou | |
| 2010/0121213 A1 | 5/2010 | Giflakis et al. | |
| 2010/0125246 A1* | 5/2010 | Kalpin .............. A61M 5/14276 | |
| | | | 702/55 |
| 2010/0137842 A1 | 6/2010 | Gibson | |
| 2010/0233021 A1 | 9/2010 | Sliwa et al. | |
| 2010/0241077 A1 | 9/2010 | Geipel et al. | |
| 2010/0294041 A1 | 11/2010 | Tai et al. | |
| 2011/0033591 A1 | 2/2011 | Henriksson | |
| 2011/0040206 A1 | 2/2011 | Burger et al. | |
| 2011/0190692 A1 | 8/2011 | Manda | |
| 2011/0208163 A1 | 8/2011 | Miesel | |
| 2011/0224603 A1 | 9/2011 | Richter | |

(56) References Cited

U.S. PATENT DOCUMENTS

2011/0290033 A1  12/2011  Flogel et al.
2011/0301575 A1  12/2011  Miesel et al.

OTHER PUBLICATIONS

Notification of Transmittal of the International Search Report and the Written Opinion of the International Searching Authority for patent application No. PCT/US2011/034068, dated Oct. 12, 2011, 17 pages.
Prosecution History from U.S. Appl. No. 12/793,457, dated Jun. 7, 2012 through Jul. 12, 2017, 334 pp.
Prosecution History from U.S. Appl. No. 15/681,957, dated Aug. 22, 2018 through Aug. 5, 2019, 17 pp.
Prosecution History from U.S. Appl. No. 12/793,459, dated Aug. 17, 2012 through Jan. 2, 2013, 21 pp.

\* cited by examiner

IMPLANTABLE MEDICAL PUMP WITH PRESSURE SENSOR

This application is a continuation application of U.S. patent application Ser. No. 15/681,957, filed Aug. 21, 2017, which is a continuation application of U.S. patent application Ser. No. 12/793,457, filed Jun. 3, 2010 and issued as U.S. Pat. No. 9,737,657 on Aug. 22, 2017. The entire contents of application Ser. Nos. 15/681,957 and 12/793,457 are incorporated herein by reference.

TECHNICAL FIELD

The disclosure relates to pressure sensors and, more particularly, to pressure sensors for use within implantable medical devices including medical pumps.

BACKGROUND

Medical pumps can be used to treat a variety of physiological, psychological, and emotional conditions. For some medical conditions, medical pumps can restore an individual to a more healthful condition and a fuller life. For example, medical pumps may be used for chronic delivery of therapeutic agents, such as drugs. As one specific example, a medical pump may be used to deliver insulin to a diabetic patient. Other examples include delivery of pain relief medication, e.g., to the intrathecal or epidural space of a patient, to alleviate chronic pain.

Some medical pumps are implantable. Implantable medical pumps are implantable medical devices (IMDs) that may be implanted at a location in the body of a patient and deliver a fluid medication through a catheter to a selected delivery site within the body of a patient. Typically, a catheter connects to an outlet of a medical pump outlet and delivers a therapeutic agent at a programmed infusion rate to a predetermined location to treat a medical condition.

An implantable medical pump may be implanted by a clinician into a patient at a location that interferes as little as practicable with patient activity. For example, implantable medical pumps are often implanted subcutaneously in the lower abdomen of a patient. Implantable medical pumps may include self-sealing fluid reservoirs accessible through ports to facilitate in-service refilling by percutaneous injection.

SUMMARY

In general, the disclosure describes an implantable medical pump with a pressure sensor. The pressure sensor may be capable of detecting pressure within a fluid enclosure, e.g., a fluid channel that directs the flow of fluid or a fluid reservoir that retains fluid, of the implantable medical pump. The pressure sensor utilizes changes in capacitance between two capacitive plates to detect changes in fluid pressure. A fluid contacting surface of the pressure sensor may also form a portion of a fluid enclosure or reservoir from which the pressure is detected. The fluid contacting surface may include a housing and a diaphragm constructed of a biocompatible and/or non-corrosive material. In some examples, this biocompatible and/or non-corrosive material is the same for both the housing and diaphragm. The housing of the pressure sensor also may have a self-aligning shape that orients the pressure sensor against an adjacent fluid enclosure wall. In some examples, this fluid enclosure wall may be a bulkhead with an opening that accepts the pressure sensor.

This capacitive pressure sensor may include, in some examples, two capacitive plates for measuring capacitance as a function of the distance between the two plates. One capacitive plate may be formed on a substantially rigid insulator, and the second capacitive plate may be a conductive diaphragm that may deflect with changes in pressure. The diaphragm may be mated to a cylindrical ferrule of the housing such that the substantially rigid insulator is sealed from the outside fluid.

In addition, in some examples, the pressure sensor may include a feedthrough pin to conduct electrical signals between the plate on the rigid insulator and a printed circuit board. The feedthrough pin may be recessed from the plane of the rigid conductive plate to prevent interfering in the capacitance between the two capacitive plates. In some cases, the feedthrough pin may terminate within a depression of the rigid insulator where the pin contacts deposited metal of the capacitive plate.

In one example an implantable medical device (IMD) is described herein. The IMD includes a fluid enclosure wall partially defining a fluid enclosure configured to accommodate a fluid within the IMD. The IMD further includes a pressure sensor comprising an operative surface configured to partially define the fluid enclosure and occlude a channel opening defined by the fluid enclosure wall.

In another example, a method is described herein. The method includes accommodating a fluid within a fluid enclosure of an implantable medical device (IMD), wherein the fluid enclosure is partially defined by a fluid enclosure wall. The method further includes detecting a pressure of the fluid with a pressure sensor comprising an operative surface configured to partially define the fluid enclosure and occlude a channel opening defined by the fluid enclosure wall.

In another example, a device is described herein. The device includes a bulkhead that defines a first portion of a fluid enclosure configured to accommodate a fluid. The device further includes a pressure sensor configured to self-align in a predetermined orientation within a channel opening defined by the bulkhead and occlude the fluid enclosure opening.

In another example a pressure sensor is described herein. The pressure sensor includes a titanium diaphragm configured as a first capacitive plate of a capacitor. The pressure sensor further includes a rigid insulator. The pressure sensor further includes a metal coating on the rigid insulator configured as a second capacitive plate of the capacitor, wherein a distance between the titanium diaphragm and the metal coating is representative of an external pressure exerted upon the titanium diaphragm.

In another example, a pressure sensor is described herein. The pressure sensor includes a first capacitive plate of a capacitor. The pressure sensor further includes a second capacitive plate of the capacitor coupled to a rigid insulator. The pressure sensor further includes an electrically conductive feedthrough pin disposed through the rigid insulator and coupled to the second capacitive plate. A first end of the feedthrough pin extends from a surface of the rigid insulator. A second end of the feedthrough pin is recessed from a capacitive surface of the second capacitive plate proximate to the first capacitive plate. The second end of the feedthrough pin is coupled to the second capacitive plate.

The details of one or more aspects of the disclosure are set forth in the accompanying drawings and the description below. Other features, objects, and advantages will be apparent from the description and drawings, and from the claims.

DETAILED DESCRIPTION

Figure 1:
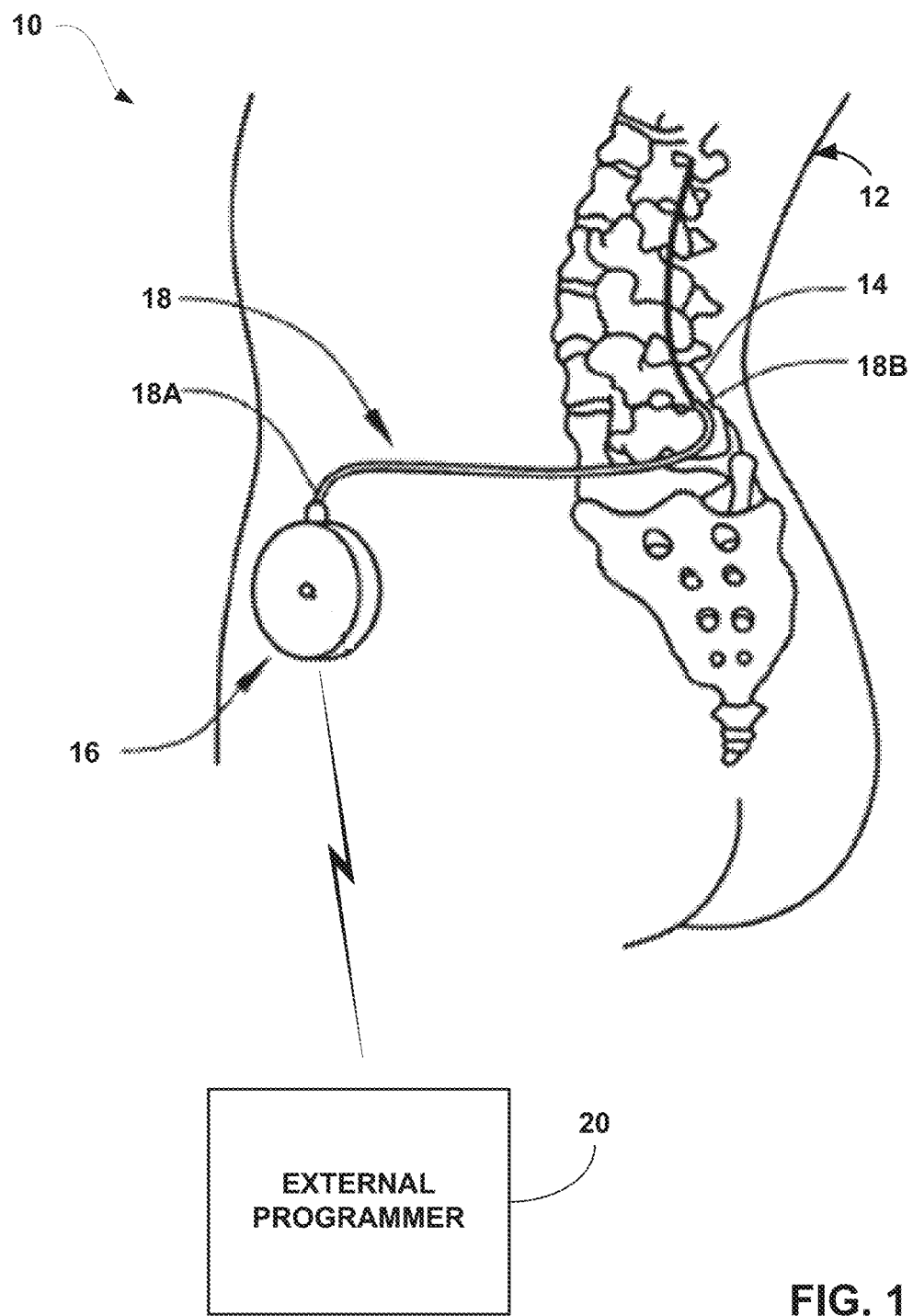
FIG. 1 is a conceptual diagram illustrating one example of a fluid delivery system that includes an implantable medical device (IMD) with a medical pump configured to deliver a therapeutic agent to a patient via a catheter.

As described herein, this disclosure is directed to a pressure sensor for use with medical devices. The pressure sensor may be a capacitive sensor that includes first and second capacitor plates, one of which may be formed as a flexible diaphragm that deflects in response to changes in pressure. The pressure sensor may include a biocompatible and/or corrosion resistant housing that houses the plates. The diaphragm may be positioned such that one surface of the diaphragm contacts fluid to be measured. In this manner, the pressure sensor forms part of a fluid enclosure that is configured to accommodate and contact fluid within an implantable medical device (IMD), such as an implantable medical pump that delivers a drug to a patient. The pressure sensor may form at least a portion of the fluid enclosure by contacting an adjacent fluid enclosure wall, for example, a fluid enclosure wall defined in a bulkhead of the IMD. In this manner, operative portions of the pressure sensor comprise at least a portion of the pressure sensor packaging instead of the pressure sensor being located within another packaging structure. The fluid enclosure may be within the bulkhead or adjacent to the bulkhead. The fluid enclosure may be utilized as a fluid channel for the transfer of fluid within the IMD or as a fluid reservoir that retains fluid within the IMD. In some examples, the pressure sensor may have a self-aligning shape and/or structure configured to receive the pressure sensor and align the sensor to a predetermined orientation within the fluid enclosure. The self-aligning shape may further serve to orient components of the sensor that provide electrical contacts for coupling with other components of the IMD, e.g., electrical circuitry.

The capacitive pressure sensor may include a first capacitive plate that is substantially rigid and a second capacitive plate that is deflectable in response to fluid pressure. The first capacitive plate may be substantially rigid in the sense that it is configured to define a static plane that acts as a reference such that a capacitance between the first and second capacitive plates may be detected. The first capacitive plate may be formed by a metal coating on a rigid insulator. The first capacitive plate may be isolated from fluid by the second capacitive plate. The second capacitive plate may be formed of a diaphragm as described above. In some examples, the second capacitive plate may be formed as a metal alloy diaphragm configured to be attached to the pressure sensor housing. The pressure sensor may operate such that fluid pressure against the second capacitive plate causes the second capacitive plate to be deflected toward the first capacitive plate, thereby causing a detectable capacitance between the plates. In one example, a feedthrough pin may be coupled to the substantially rigid capacitive plate recessed from the capacitive plane of the plate. The feedthrough pin may couple the first capacitive plate to a printed circuit board or other circuitry of the pressure sensor. The second capacitive plate may be electrically coupled to the printed circuit board via a housing of the pressure sensor.

The techniques of this disclosure are also directed to the assembly of a pressure sensor. In one example, the pressure sensor includes a housing ferrule configured to receive the first capacitive plate described above. The housing ferrule may include at least one protrusion defined within the housing ferrule. The at least one protrusion may present a support structure for the mounting of the first, substantially rigid, capacitive plate within the housing ferrule. For example, the at least one protrusion may provide a mounting point for affixing the first capacitive plate via welding or otherwise. The at least one protrusion may be a single protrusion, a set of protrusions, an annular ring, a lip, or other structure. The at least one protrusion may define a smaller diameter than a diameter of the housing ferrule, such that a gap is created between the housing ferrule and a support structure coupled to the first capacitive plate. The defined gap may to allow the support structure to tilt within the housing ferrule such that the capacitive plate can be positioned in a plane parallel to an edge of the housing ferrule. In one example, where the first, substantially rigid capacitive plate is formed of a metal coating on a rigid insulator, it may be desirable to tilt the support structure relative to the housing to compensate for any discrepancy in a thickness of the metal coating. An assembly tool may be used to facilitate the positioning of the rigid capacitive plate by providing a stage at a fixed height within the housing ferrule. Once the support structure is affixed in a secure position within the ferrule, the assembly tool can be removed to allow the second capacitive plate (e.g., flexible diaphragm) to be attached to the distal edge of the housing ferrule.

The pressure sensor described herein may be used in several capacities within the IMD. For example, the pressure sensor may be used to monitor the fluid pressure of a refill port when fluid is being added to the IMD reservoir. In another example, the pressure sensor may be used to monitor the pressure of fluid exiting the IMD and being delivered to a patient. As an additional example, the pressure sensor may be positioned to detect the pressure of a fluid within a reservoir retaining the fluid within the IMD. Further, two or more pressure sensors may be used to monitor fluid pressure at several locations within the IMD. As described herein, the fluid may generally in liquid form. Although generally described for use within an implantable medical device, it is contemplated that the pressure sensor described herein may be used in any other type of medical or non-medical systems or devices.

FIG. 1 is a conceptual diagram illustrating one example of a therapy system 10 including an exemplary IMD 16 configured to deliver at least one therapeutic agent, such as a pharmaceutical agent, insulin, pain relieving agent, anti-inflammatory agent, gene therapy agent, or the like, to a target site within patient 12. The therapeutic agent may be delivered via a catheter 18 coupled to IMD 16. In one example, catheter 18 may comprise a plurality of catheter segments. In other examples, catheter 18 may be a unitary catheter. In the example shown in FIG. 1, the target site for fluid delivery is proximate to spinal cord 14 of patient 12. A proximal end 18A of catheter 18 is coupled to IMD 16, while a distal end 18B of catheter 18 is located proximate to the target site. Therapy system 10 also includes external programmer 20, which wirelessly communicates with IMD 16 as needed, such as to provide or retrieve therapy information or control aspects of therapy delivery (e.g., modify the therapy parameters, turn IMD 16 on or off, receive warnings or alerts, and so forth). While patient 12 is generally referred to as a human patient, other mammalian or non-mammalian patients are also contemplated.

Generally, IMD 16 has an outer housing that is constructed of a biocompatible material that resists corrosion and degradation from bodily fluids, such as titanium or biologically inert polymers. IMD 16 may be implanted within a subcutaneous pocket close to the therapy delivery site. For example, in the example shown in FIG. 1, IMD 16 is implanted within an abdomen of patient 12. In other examples, IMD 16 may be implanted within other suitable sites within patient 12 which may depend, for example, on the target site within patient 12 for the delivery of the therapeutic agent.

IMD 16 includes a medical pump that delivers fluid from a reservoir of the IMD to patient 12. As described herein, one or more pressure sensors may be employed within the IMD to monitor and detect pressures of fluid within IMD 16. The pressure sensors may detect static pressures along with pressure waves created when fluid is added or removed from the IMD. The pressure sensors may then provide information about the quantity of fluid remaining within the IMD or delivered by the IMD.

Catheter 18 may be coupled to IMD 16 either directly or with the aid of a catheter extension (not shown in FIG. 1). In the example shown in FIG. 1, catheter 18 traverses from the implant site of IMD 16 to one or more target sites proximate to spine 14. Catheter 18 may be positioned such that one or more fluid delivery outlets of catheter 18 are proximate to the one or more target sites within patient 12. IMD 16 may deliver a therapeutic agent to the one or more target sites proximate to spinal cord 14 with the aid of catheter 18. For example, IMD 16 may be configured for intrathecal drug delivery into the intrathecal space or epidural space surrounding spinal cord 14. The intrathecal space is within the subarachnoid space of spinal cord 14, which is past the epidural space and dura mater and through the theca of spinal cord 14.

Therapy system 10 may be used, for example, to reduce pain experienced by patient 12. IMD 16 may deliver one or more therapeutic agents to patient 12 according to one or more dosing programs that set forth different therapy parameters, such as a therapy schedule specifying programmed doses, dose rates for the programmed doses, and specific times to deliver the programmed doses. The dosing programs may be a part of a program group for therapy, where the group includes a plurality of dosing programs and/or therapy schedules. In some examples, IMD 16 may be configured to deliver a therapeutic agent to patient 12 according to different therapy schedules on a selective basis. IMD 16 may include a memory to store one or more therapy programs, instructions defining the extent to which patient 12 may adjust therapy parameters, switch between dosing programs, or undertake other therapy adjustments. Patient 12 may select and/or generate additional dosing programs for use by IMD 16 via external programmer 20 at any time during therapy or as designated by a clinician.

In some examples, multiple catheters 18 may be coupled to IMD 16 to target the same or different tissue or nerve sites within patient 12. Thus, although a single catheter 18 is shown in FIG. 1, in other examples, system 10 may include multiple catheters or catheter 18 may define multiple lumens for delivering different therapeutic agents to patient 12 or for delivering a therapeutic agent to different tissue sites within patient 12. Accordingly, in some examples, IMD 16 may include a plurality of reservoirs for storing more than one type of therapeutic agent. With multiple reservoirs, IMD 16 may include separate pressure sensors to monitor the fluid in each reservoir. In some examples, IMD 16 may include a single long tube that contains the therapeutic agent in place of a reservoir. However, for ease of description, an IMD 16 including a single reservoir is primarily discussed herein with reference to the example of FIG. 1.

Programmer 20 may be an external computing device configured to wirelessly communicate with IMD 16. For example, programmer 20 may be a clinician programmer that the clinician uses to communicate with IMD 16. Alternatively, programmer 20 may be a patient programmer that allows patient 12 to view and modify therapy parameters. The clinician programmer may include additional or alternative programming features, relative to the patient programmer. For example, more complex or sensitive tasks may only be allowed by the clinician programmer to prevent patient 12 from making undesired changes to the operation of IMD 16.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured to an application to simulate programmer 20. Alternatively, a notebook computer, tablet computer, or other personal computer may execute an application to function as programmer 20, e.g., with a wireless adapter connected to the personal computer for communicating with IMD 16.

A clinician may use programmer 20 to program IMD 16 with one or more therapy programs that define the therapy delivered by IMD 16. During a programming session, the clinician may determine one or more dosing programs that may provide effective therapy to patient 12. Patient 12 may provide feedback to the clinician as to the efficacy of a specific program being evaluated or desired modifications to the dosing program. Once the clinician has identified one or more programs that may be beneficial to patient 12, patient 12 may continue the evaluation process and determine which dosing program or therapy schedule best alleviates the condition of patient 12 or otherwise provides efficacious therapy to patient 12.

The dosing program information may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive supplemental doses such as patient-initiated doses (e.g., a lock-out interval), a maximum dose that may be delivered over a given time interval, and so forth. IMD 16 may include a feature that prevents dosing the therapeutic agent in a manner inconsistent with the dosing program. Programmer 20 may assist the clinician in the creation/identification of dosing programs by providing a methodical system of identifying potentially beneficial therapy parameters.

A dosage of a therapeutic agent, such as a drug, may be expressed as an amount of drug, e.g., measured in milligrams, provided to the patient over a particular time interval, e.g., per day or twenty-four hour period. This dosage amount may convey to the caregiver an indication of the probable efficacy of the drug and the possibility of side effects of the drug. In general, a sufficient amount of the drug should be administered in order to have a desired therapeutic effect, such as pain relief. However, the amount of the drug administered to the patient may be limited to a maximum amount, such as a maximum daily dose, in order not to avoid potential side effects. Program information specified by a user via programmer 20 may be used to control dosage amount, dosage rate, dosage time, maximum dose for a given time interval (e.g., daily), or other parameters associated with delivery of a drug or other fluid by IMD 16.

In some cases, programmer 20 may also be configured for use by patient 12. When configured as a patient programmer, programmer 20 may have limited functionality in order to prevent patient 12 from altering critical functions or applications that may be detrimental to patient 12. In some cases, a patient programmer may permit the patient to control IMD 16 to deliver a supplemental, patient-initiated dose, if permitted by the applicable therapy program administered by the IMD, e.g., if delivery of a patient-initiated dose would not violate a lockout interval or maximum dosage limit.

Programmer 20 may also provide an indication to patient 12 when therapy is being delivered or when IMD 16 needs to be refilled or when the power source within programmer 20 or IMD 16 need to be replaced or recharged.

Programmer 20 may also provide warnings or alerts to the clinician or patient to indicate when there is a problem with an aspect of IMD 16. For example, programmer 20 may provide a visual and/or audible alert when the pressure sensor detects beyond threshold pressure near the refill port. In this manner, the clinician may avoid damaging fluid enclosures, the pressure sensor, or other components of IMD 16 as well as preventing an overflow of drug into patient 12. In another example, programmer 20 may relay an alert when the pressure sensor detects above threshold pressures within the fluid enclosure that indicate a blockage to the delivery of drug to patient 12.

Programmer 20 may also alert a user that an unauthorized removal of fluid has occurred. For example, the pressure sensor may be capable of detecting movement or changes in the quantity of the fluid separate from the operation of the medical pump. In this manner, IMD 16 may be able to identify when fluid has been removed from IMD 16 without an instructed or authorized delivery of fluid to patient 12. IMD 16 may transmit the alert to programmer 20, and programmer 20 may present the alert to a user, e.g., a clinician. Whether external programmer 20 is configured for clinician or patient use, programmer 20 may communicate to IMD 16 or any other computing device via wireless communication. Programmer 20, for example, may communicate via wireless communication with IMD 16 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 16 and another programmer via remote telemetry techniques known in the art, communicating via a local area network (LAN), wide area network (WAN), public switched telephone network (PSTN), or cellular telephone network, for example.

In other applications of therapy system 10, the target therapy delivery site within patient 12 may be a location proximate to sacral nerves (e.g., the S2, S3, or S4 sacral nerves) in patient 12 or any other suitable nerve, organ, muscle or muscle group in patient 12, which may be selected based on, for example, a patient condition. For example, therapy system 10 may be used to deliver a therapeutic agent to tissue proximate to a pudendal nerve, a perineal nerve or other areas of the nervous system, in which cases, catheter 18 would be implanted and substantially fixed proximate to the respective nerve. As further examples, catheter 18 may be positioned to deliver a therapeutic agent to help manage peripheral neuropathy or post-operative pain mitigation, ilioinguinal nerve therapy, intercostal nerve therapy, gastric stimulation for the treatment of gastric motility disorders and/or obesity, muscle stimulation, for mitigation of other peripheral and localized pain (e.g., leg pain or back pain). As another example, catheter 18 may be positioned to deliver a therapeutic agent to a deep brain site or within the heart (e.g., intraventricular delivery of the agent). Delivery of a therapeutic agent within the brain may help manage any number of disorders or diseases. Example disorders may include depression or other mood disorders, dementia, obsessive-compulsive disorder, migraines, obesity, and movement disorders, such as Parkinson's disease, spasticity, and epilepsy. Catheter 18 may also be positioned to deliver insulin to a patient with diabetes.

Examples of therapeutic agents that IMD 16 may be configured to deliver include, but are not limited to, insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics.

Figure 2:
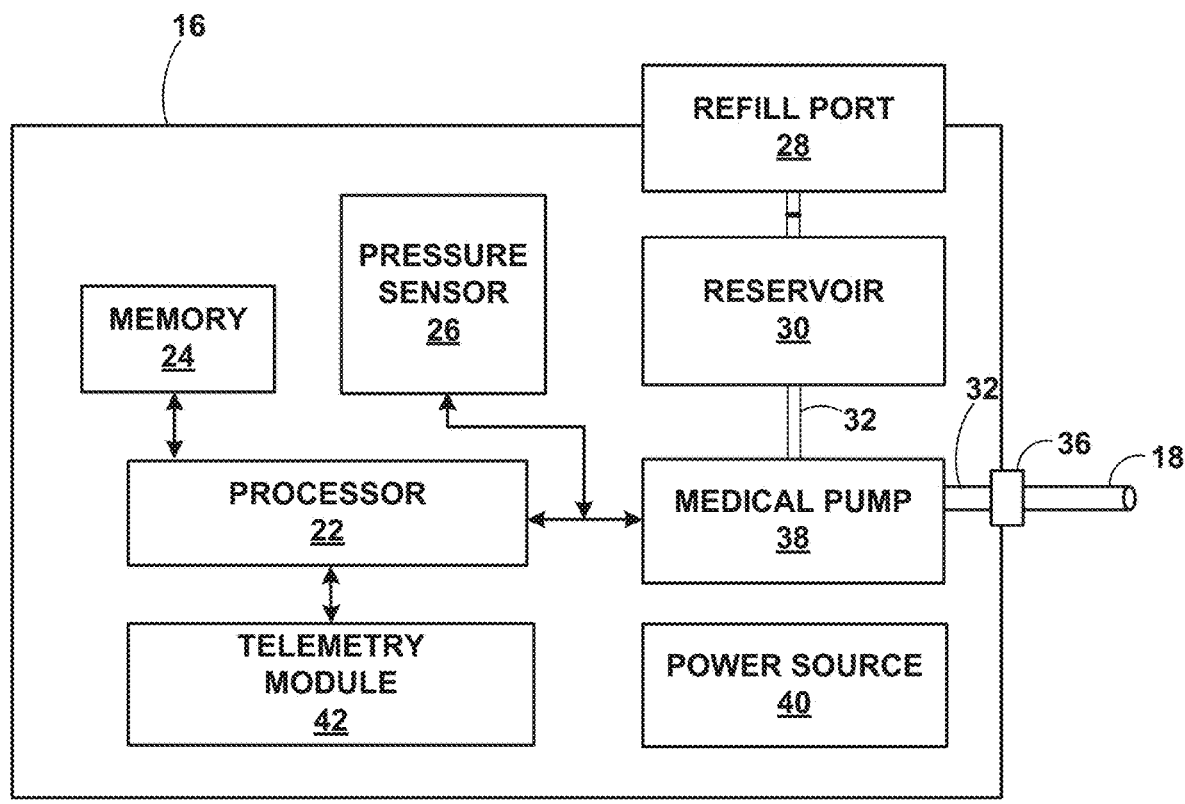
FIG. 2 is a functional block diagram illustrating an exemplary IMD with a medical pump.

FIG. 2 is a functional block diagram illustrating components of an example of IMD 16, which includes processor 22, memory 24, pressure sensor 26, refill port 28, reservoir 30, internal tubing 32, catheter outlet 36, medical pump 38, power source 40, and telemetry module 42. Medical pump 38 may be a mechanism that delivers a therapeutic agent in some metered or other desired flow dosage to the therapy site within patient 12 from reservoir 30 via the catheter 18. Refill port 28 may comprise a self-sealing injection port. The self-sealing injection port may include a self-sealing membrane to prevent loss of therapeutic agent delivered to reservoir 30 via refill port 28. After a delivery system, e.g., a hypodermic needle, penetrates the membrane of refill port 28, the membrane may seal shut when the needle is removed from refill port 28. Internal tubing 32 may be a segment of tubing that runs from reservoir 30, around or through medical pump 38 to catheter outlet 36. Internal tubing 32 may be constructed of any materials capable of forming a fluid path or fluid enclosure, such as cavities within metal structures or adjoined structures that form continuous surfaces to accommodate fluid.

Pressure sensor 26 may monitor a pressure of fluid within a fluid enclosure of IMD 16. This fluid enclosure may be part of internal tubing 32, e.g., adjacent to catheter outlet 36, reservoir 30, or refill port 28. In the example of FIG. 2, pressure sensor 26 is positioned to create a portion of the fluid enclosure defining reservoir 30. In this manner, pressure sensor 26 includes diaphragm that contacts the fluid within reservoir 30 and seals electrical components from the fluid. The diaphragm operates as one capacitive plate of the pressure detecting capacitor. Circuitry of IMD 16 may detect changes in fluid pressure based on a detected change in capacitance between the diaphragm and another capacitive plate contained within a housing of pressure sensor 26. Pressure sensor 26 may utilize energy from a power source 40 to cause an electrical potential between the diaphragm and substantially rigid capacitor plate.

As pressure sensor 26 detects changes in capacitance from diaphragm deflection, pressure sensor 26 may communicates with a processor 22 and/or other circuitry to transmit data or signals (e.g., indicative of a detected capacitance) representative of detected fluid pressure. In one example, a flex circuit (not shown) may be used to electrically couple pressure sensor 26 to processor 22. Processor 22 may accordingly adjust IMD 16 function or transmit information to a user based upon received information indicative of detected fluid pressure. In addition, medical pump 38 may communicate directly to pressure sensor 26 to retrieve pressure information.

In the example of FIG. 2, pressure sensor 26 delivers pressure information to processor 22 periodically or upon request by processor 22. Pressure sensor 26 may internally calibrate the measured capacitance values and output a voltage, or digital, signal indicative of a detected pressure. Processor 22 may then use this signal to identify the detected pressure at the diaphragm. In one example, an analog to digital converter of IMD 16 may convert an analog voltage signal indicative of detected pressure from pressure sensor 26 to a digital value representative of the detected fluid pressure. Processor 22 may process this digital value and apply an algorithm or look-up table to generate calibrated pressure of the fluid. This processed pressure value may then be usable by software controlling operation of IMD 16 via processor 22.

Pressure sensor 26 may convert detected capacitance between the rigid capacitor plate and the diaphragm capacitor plate differently than conventional parallel plate capacitors due to the shape of the diaphragm with fully constrained edges. In the example of a circular diaphragm as described herein, the capacitance gap is the smallest at the center and increased toward the diaphragm edge. Factors such as the ambient temperature, permittivity of free space, in-plane tension on the diaphragm, elasticity of the diaphragm material, diaphragm thickness, and the radius of the rigid capacitor may relevant to the measured capacitance. Some of these factors may be less relevant with non-circular diaphragms. In other examples, capacitance measurements may be developed experimentally to create a formula or look-up table that determines pressure-capacitance relationships. This look-up table or formula may be stored in pressure sensor 26 or in memory 24.

Although only a single pressure sensor 26 is depicted in the example of FIG. 2, multiple pressure sensors may be provided within IMD 16. In one example, the multiple pressure sensors may be positioned to detect pressure within different fluid enclosures. For example, a pressure sensor may be positioned within a fluid channel between refill port 28 and reservoir 30 and another pressure sensor may be positioned within a fluid channel between medical pump 38 and catheter outlet 36. In another example, a pressure sensor may be positioned within a fluid enclosure that creates reservoir 30, a second pressure sensor may be positioned within a fluid channel adjacent refill port 28, and a third pressure sensor may be positioned within a fluid channel adjacent catheter outlet 36. These and other multiple pressure sensor configurations are contemplated with the pressure sensor disclosed herein. Alternatively, multiple pressure sensors may be placed within the same fluid enclosure in order to provide redundant sensors in the case of a malfunction. Further, multiple pressure sensors may be utilized within the same fluid enclosure to provide more detailed information indicative of detected pressure that may be capable of identifying a quantity or velocity of a fluid dispensed by medical pump 38. Any pressure sensors within IMD 16 may be monitored and/or controlled by processor 22 and/or other circuitry of IMD 16.

In other examples, pressure sensor 26 may employ two or more capacitors for detecting fluid pressure at different locations within one fluid enclosure or multiple different fluid enclosures. In this manner, pressure sensor 26 may include multiple diaphragms that each form a capacitive pressure sensor with an associated substantially rigid capacitive plate.

Processor 22 may controls the operation of medical pump 38 with the aid of instructions associated with program information that is stored in memory 24. For example, the instructions may define dosing programs that specify an amount of a therapeutic agent to be delivered to a target tissue site within patient 12 from reservoir 30 via catheter 18. The instructions may further specify a time at which the agent will be delivered and the time interval over which the agent will be delivered. The amount of the agent and the time over which the agent will be delivered may be functions of a dosage rate at which fluid is delivered. In other examples, a quantity of the agent may be delivered according to one or more physiological characteristics of a patient, e.g., physiological characteristics sensed by one or more sensors (not shown) implanted within a patient as part of therapy system 10 (FIG. 1). Components described as processors within IMD 16 and external programmer 20 may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 24 may include any volatile or non-volatile media, such as a random access memory (RAM), read only memory (ROM), non-volatile RAM (NVRAM), electrically erasable programmable ROM (EEPROM), Flash memory, and the like. As mentioned above, memory 24 may store program information including instructions for execution by processor 22, such as, but not limited to, therapy programs, historical therapy programs, timing programs for delivery of fluid from reservoir 30 to catheter 18, and any other information regarding therapy of patient 12. In addition, memory 24 may store instructions for the operation of pressure sensor 26, such as maximum pressure thresholds, calibration algorithms, and capacitance formulas. Further, memory 24 may contain instructions for operations upon certain fluid pressures being detected. Memory 40 may include separate memories for storing instructions, patient information, therapy parameters (e.g., grouped into sets referred to as "dosing programs"), therapy adjustment information, program histories, and other categories of information such as any other data that may benefit from separate physical memory modules.

Telemetry module 42 in IMD 16, as well as telemetry modules in a controller, such as programmer 20, may accomplish communication by RF communication techniques. In addition, telemetry module 42 may communicate with programmer 20 via proximal inductive interaction of IMD 16 with external programmer 20. In one example, processor 22 controls telemetry module 42 to send and receive information.

Power source 40 delivers operating power to various components of IMD 16. Power source 40 may include a small rechargeable or non-rechargeable battery and a power generation circuit to produce the operating power. In the case of a rechargeable battery, recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time. As a further alternative, an external inductive power supply may transcutaneously power IMD 16 whenever measurements are needed or desired.

Figure 3:
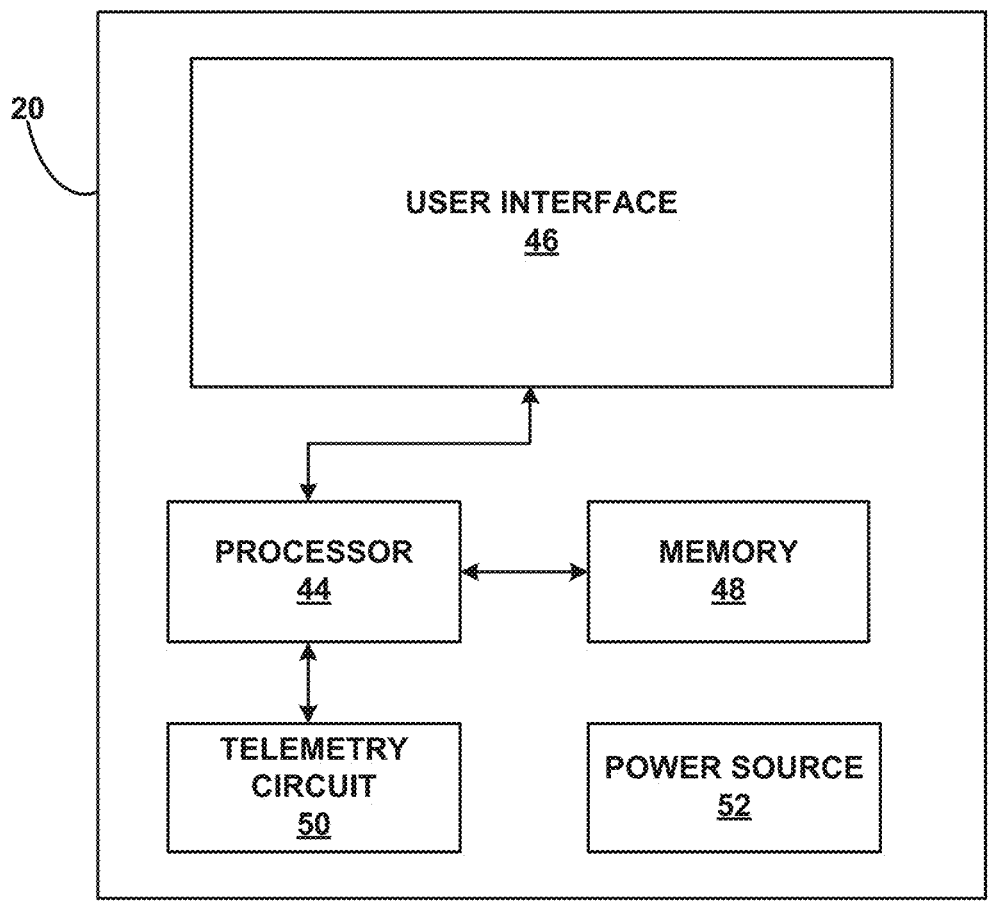
FIG. 3 is a functional block diagram illustrating an exemplary external programmer that communicates with an IMD.

FIG. 3 is a functional block diagram illustrating various components of an example external programmer 20 for IMD 16. As shown in FIG. 3, external programmer 20 is an external display device that includes processor 44, memory 48, telemetry circuit 50, user interface 46, and power source 52. External programmer 20 may be embodied as a patient programmer or clinician programmer. A clinician or patient 12 interacts with user interface 46 in order to manually change the stimulation parameters of a program, change programs within a group, view therapy information, receive warnings or alerts, or otherwise interact with and control IMD 16. Generally, external programmer 20 configured as a clinician programmer have include additional features not provided on the patient programmer.

User interface 46 may include a screen or display and one or more input buttons that allow external programmer 20 to receive input from a user. Alternatively, user interface 46 may additionally or only utilize a touch screen display. The screen may be a liquid crystal display (LCD), dot matrix display, organic light-emitting diode (OLED) display, touch screen, or any other device capable of delivering and/or accepting information. For audible and/or tactile indications, such as an above threshold pressure, external programmer 20 may further include one or more audio speakers, voice synthesizer chips, piezoelectric buzzers, or the like.

Input buttons for user interface 46 may include a touch pad, increase and decrease buttons, emergency shut off button, and other buttons needed to control the delivery of drug therapy. Processor 44 controls user interface 46, retrieves data from memory 48 and stores data within memory 48. Processor 44 also controls the transmission of data through telemetry circuit 50 to IMD 16. Memory 48 includes operation instructions for processor 44 and data related to patient 12 therapy.

Telemetry circuit 50 allows the transfer of data to and from IMD 16. Telemetry circuit 50 may communicate with IMD 16 in real-time during drug refill or certain communication tasks. For example, IMD 16 may immediately transmit an alert if pressure sensor 26 indicates an above threshold pressure in reservoir 30 that could be indicative of a blockage in catheter 18.

In addition, telemetry circuit 50 may communicate at a scheduled time or when the telemetry circuit detects the proximity of IMD 16. User interface 46 may then update displayed information accordingly. Alternatively, telemetry circuit 50 may communicate with IMD 16 when signaled by a user through user interface 46. To support RF communication, telemetry circuit 50 may include appropriate electronic components, such as amplifiers, filters, mixers, encoders, decoders, and the like. Power source 52 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 16 in addition to programming IMD 16. Alternatively, a recharging device may be capable of communication with IMD 16. Then, the recharging device may be able to transfer programming information, data, or any other information described herein to IMD 16. In this manner, the recharging device may be able to act as an intermediary communication device between external programmer 20 and IMD 16. In other cases, programmer 20 may be integrated with a recharging functionality in the combined programming/recharging device. The techniques described herein may be communicated between IMD 16 via any type of external device capable of communication with IMD 16.

Figure 4:
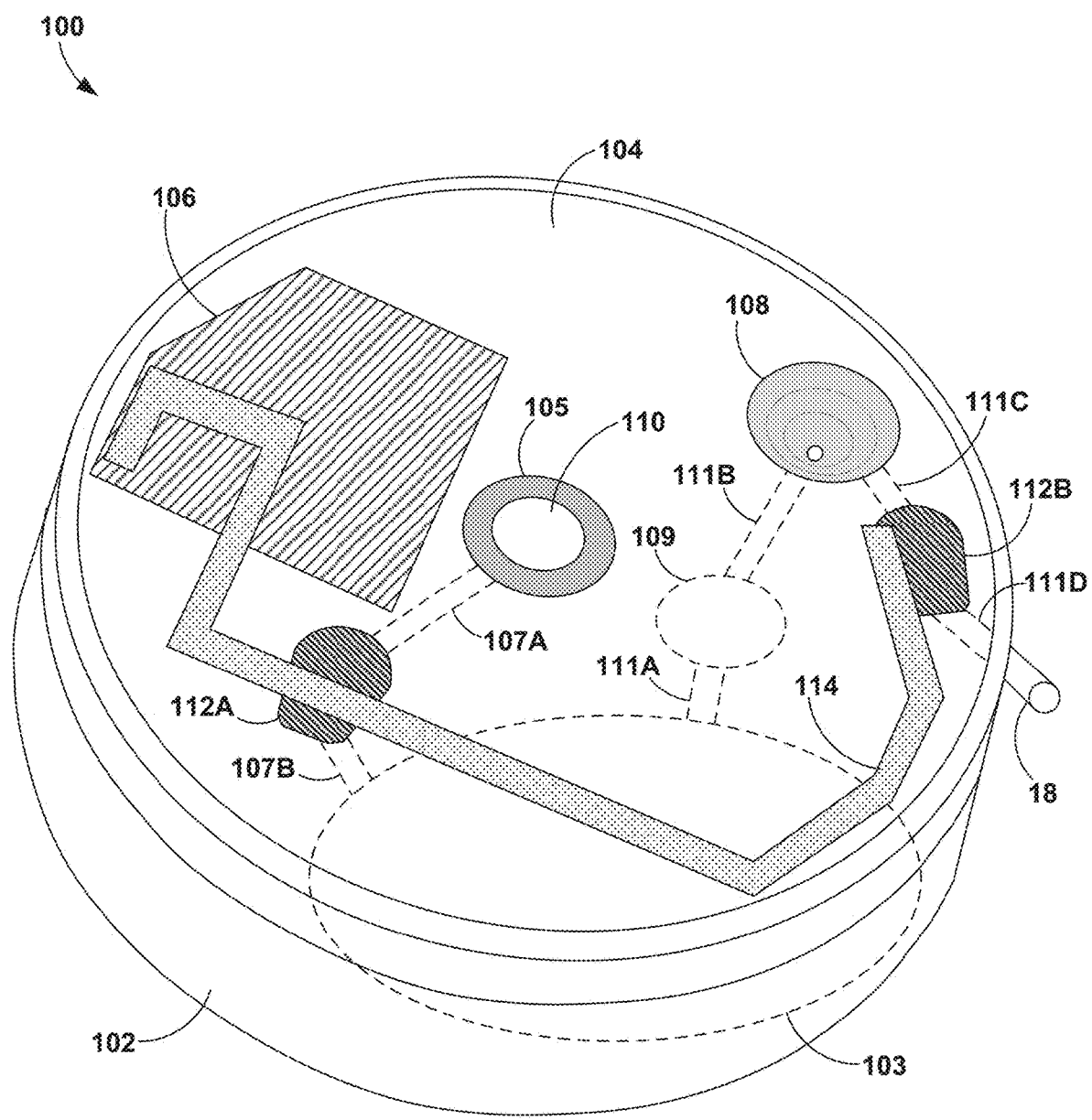
FIG. 4 is a conceptual diagram illustrating one example of an IMD bulkhead configured to receive a pressure sensor consistent with this disclosure.

FIG. 4 is a conceptual diagram illustrating one example of a bulkhead 104 of IMD 100. IMD 100 is similar to IMD 16 of FIGS. 1 and 2, but FIG. 4 shows selected components housed within an exposed bulkhead 14. The example of FIG. 4 shows that IMD 100 includes reservoir back housing 102, bulkhead 104, circuitry 106, refill port 105, refill opening 110, catheter access port 108, pressure sensors 112A and 112B (collectively "pressure sensors 112"), flexible circuit 114, and catheter 18. A bulkhead cover (not shown) has been removed to show these components. The bulkhead cover may be provided to seal the electrical components from body fluids and tissues of patient 12. In some examples, the bulkhead cover may be integrated with bulkhead 104.

In addition, some components that are hidden under bulkhead 104 are also shown using dotted lines. These components describe an example fluid path within the example of FIG. 4. Fluid channel 107A provides a path for fluid between refill port 105 and pressure sensor 112A. Fluid channel 107BA provides a path for fluid between pressure sensor 112A and reservoir 103. Together, fluid channels 107A and 107B (collectively "fluid channel 107") create a fluid path for fluid to refill reservoir 103. Fluid channel 107A may be a fluid enclosure that is a portion of a receptacle for receiving fluid within IMD 100. Pressure sensor 112A thus detects the pressure of fluid between refill port 105 and reservoir 103.

Fluid channels 111A, 111B, 111C, and 111D (collectively "fluid channels 111") create a fluid path for fluid to be dispensed from reservoir 103 and delivered to patient 12. Fluid channel 111A connects reservoir 103 to medical pump 109. Fluid channel 111B provides a fluid path between medical pump 109 and catheter access port 108. Fluid channel 111C provides a fluid path between catheter access port 108 and pressure sensor 112B, and fluid channel 111D provides a fluid path between pressure sensor 112B and catheter 18, via the catheter outlet (not shown). Pressure sensor 112B thus detects the pressure of fluid between medical pump 109 and catheter 18. In other examples of IMD 100, a pressure sensor may also be positioned to detect the pressure of the fluid within reservoir 103. In this manner, a fluid enclosure may take on different forms. Fluid channels 107 and 111 are both fluid enclosures that allow a fluid to flow through the structure. Conversely, reservoir 103 may be a fluid enclosure that is configured to retain or store fluid for later delivery to patient 12.

Reservoir back housing 102 encloses the portion of IMD 100 that retains a fluid, e.g., a delivered medication, within IMD 100. Reservoir back housing 102 may also be mated to bulkhead 104 to form hermetic seal of IMD 100. The hermetic seal may isolate components of IMD 100 from the environment in which IMD 100 is disposed. Bulkhead 104 may also form a portion of a fluid enclosure wall that contacts fluid within the reservoir. Bulkhead 104 may also form a portion of an external surface of IMD 100 that contacts patient 12 tissues when implanted.

Bulkhead 104 may house functional components of IMD 100. For example, bulkhead 104 may include refill port 105 and refill opening 110 to accept a syringe to replenish a drug to be later delivered to patient 12. Refill opening 110 may help to guide a syringe into a diaphragm that accepts a needle of the syringe to aid the clinician in refilling IMD 100 when IMD is disposed within patient 12.

Pressure sensors 112 of FIG. 4 illustrate examples of pressure sensor 26 as illustrated in FIG. 2. Pressure sensors 112 may be mounted within openings defined by bulkhead 104 to form a portion of a fluid enclosure in which each pressure sensor 112 detects fluid pressure. Pressure sensor 112A may be positioned to define at least a portion of fluid channel 107 that directs fluid between refill port 105 and reservoir 103 of IMD 100, and pressure sensor 112B may be positioned to define the fluid channel 111 that directs fluid between medical pump 109 and catheter 18 of IMD 100. When fluid is added within refill opening 110, the fluid passes through channel 107 and into reservoir 103.

In one example, pressure sensors 112 are identical to each other in size and shape as well as pressure sensing function. In other examples, pressure sensors 112 may be of different size, shape, and/or pressure sensing function. In examples where pressure sensor 112A may be identical to pressure sensor 112B, either pressure sensor can be used at each location, thereby simplifying and construction of IMD 100. In one example, one or both of pressure sensors 112 may also have a self-aligning shape that positions each pressure sensor in a predetermined orientation within the channel opening of bulkhead 104. The self-aligning shape of each pressure sensor 112 may also facilitate electrical contact between pressure sensors 112 and flexible circuit 114 for coupling of pressure sensors 112 to one or more circuits of IMD 100, e.g., circuit 106 depicted in FIG. 4. In other words, the predetermined orientation may position one or more electrical contacts of one or more of pressure sensors 112 in proximity to flexible circuit 114 for electrical coupling to circuitry 106 and/or other circuitry of IMD 100. Flexible circuit 114 as described herein may by any structure capable of transferring electrical energy, e.g., signal indicative of detected pressure measurements. For example, flex circuit 114 may be a PC board trace, electrically conductive tape, or any other like structure.

Circuitry 106 may recognize in which fluid enclosure each of pressure sensors 112 detects fluid pressure within IMD 16 based upon which connection channel of flexible circuit 114 each pressure sensor uses. Circuitry 106 may include a processor and memory, e.g., processor 22 and memory 24 of IMD 16 in FIG. 2, and communicate with one or more of pressure sensors 112, e.g., to receive one or more indications of fluid pressure measurements. Flexible circuit 114 may be electrically coupled to circuitry 106 and/or pressure sensors 112. Flexible circuit 114 may be configured to connect with the electrical connections of pressure sensors 112, and flexible circuit 114 may include separate channels for communications between circuitry 106 and pressure sensors 112.

Other components may also be provided within bulkhead 104. For example, bulkhead 104 may house a telemetry circuit, a power supply, a medical pump, and other components desirable for the deliver drug therapy to patient 12.

Figure 5A:
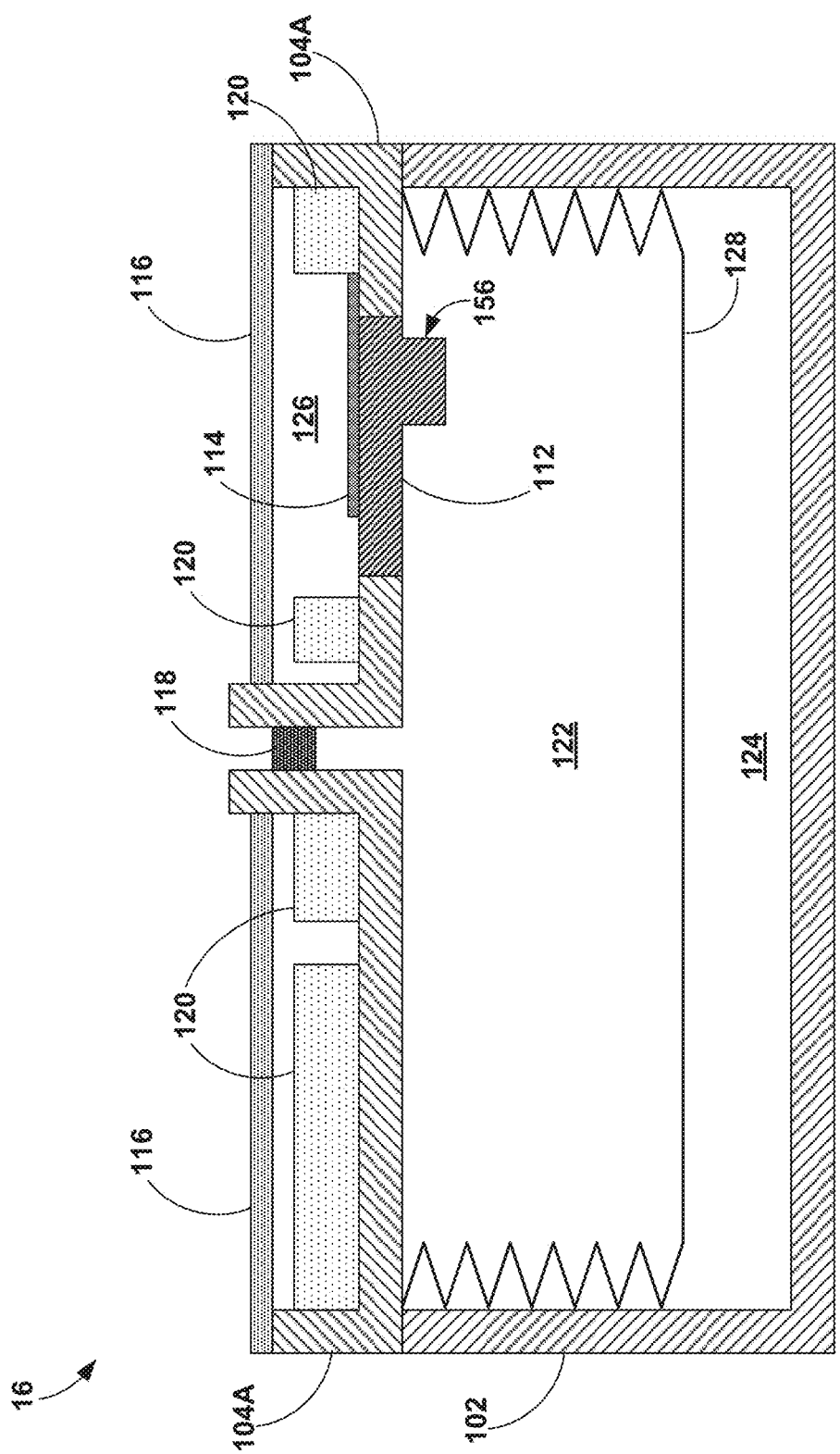
FIG. 5A is a conceptual diagram illustrating a cross-section of another example of an IMD that includes a fluid enclosure defined by a pressure sensor and a bulkhead of an IMD consistent with this disclosure.

FIG. 5A is a conceptual diagram illustrating a cross-section of one example of an IMD 16 that includes a pressure sensor 112. As shown in FIG. 5A, IMD 16 includes reservoir back housing 102, bulkhead 104, pressure sensor 112, flexible circuit 114, top shield 116, valve 118, and components 120. Pressure sensor 112 may be any pressure sensor described herein, such as the example pressure sensor 26 depicted in FIG. 2. Components 120 may include various electrical and structural components required for the function of IMD 16, such as a processor, power supply, memory, telemetry circuitry, and medical pump controls. The medical pump that delivers fluid from IMD 16 is not shown in FIG. 5A.

Reservoir back housing 102 may be mated and/or sealed to bulkhead 104. Bulkhead 104 may define a fluid enclosure wall, or a portion of a fluid enclosure wall, that defines a portion of reservoir 122 accommodating or retaining the fluid. Reservoir 122 is an example fluid enclosure that contains, retains or channels fluid within IMD 16. Reservoir 122 may be defined by pressure sensor 112 and reservoir bellows 128. In one example, pressure sensor 112 includes an operative surface that contacts a fluid within reservoir 122 and attaches to bulkhead 104 to form a continuous surface. In this manner, pressure sensor 112 may physically contact bulkhead 104 or attach to bulkhead 104 with a weld or other mechanism for completing a surface defining reservoir 122. Reservoir bellows 128 may expand and contract in response to a volume of fluid accommodated by reservoir 122. Remaining capacity 124 is the space between reservoir bellows 128 and reservoir back housing 102. In one example, reservoir bellows 128 may be constructed of a folding structure that unfolds to increase the volume of fluid accommodated by channel 122. Alternatively, reservoir bellows 128 is an elastic barrier made of a polymer or other flexible biocompatible and/or non-corrosive material that allows fluid to be removed from reservoir 122 and delivered to patient 12. In other examples, reservoir 128 may be partially defined by another structure different than reservoir bellows 128. In some examples, a propellant or other gas may reside in remaining capacity 124 to provide back pressure to reservoir bellows 128.

Valve 118 may positioned within bulkhead 104 and configured to fully enclose reservoir 122. Valve 118 may be controlled to allow fluid to enter medical pump 38 (not shown). Alternatively, valve 118 may be part of a medical pump 38 that allows fluid to leave reservoir 122 and be delivered to patient 12. In other examples of IMD 16, medical pump 38 may function as valve 118 by only allowing fluid to leave reservoir 122 upon operation of medical pump 38. In any case, valve 118 may operate to close reservoir 122 defined by bulkhead 104 and pressure sensor 112.

Pressure sensor 112 may be configured to detect the pressure of fluid retained within reservoir 122. Since the deformable diaphragm (not shown in FIG. 5A) of pressure sensor 112 forms a portion of the fluid enclosure wall defining reservoir 122, pressure sensor 112 is capable of detecting a pressure of fluid within reservoir 122 or any pressure change caused by the addition or removal of fluid from the fluid enclosure. Pressure sensor 112 may also have a self-aligning shape to occlude, and reside at least partially within, a channel opening in bulkhead 104. Although pressure sensor 112 may fully occlude the channel opening when inserted, other examples may require pressure sensor 112 to be welded at the joint between bulkhead 104 and pressure sensor 112 before the channel opening is fully occluded to form a sealed barrier to fluid. As shown in FIG. 5A, the channel opening is defined by bulkhead 104 where pressure sensor 112 resides. The channel opening may be sized and/or shaped to only accept pressure sensor 112 in a predetermined orientation. In another example, the channel opening may include a keyed structure to only accept pressure sensor 112 in a predetermined orientation. Upon the installation of pressure sensor 112 into bulkhead 104, reservoir 122 is completed, i.e., pressure sensor 112 forms at least one surface of reservoir 122.

In the example of FIG. 5A, pressure sensor 112 includes housing ferrule 156 which provides an attachment structure for the diaphragm and an enclosure for a rigid capacitive plate. Housing ferrule 156 as depicted in FIG. 5A is substantially cylindrical, however other shapes (e.g., oval, square, rectangular, other) are also contemplated and consistent with this disclosure. As depicted in FIG. 5A, housing ferrule 156 extends from bulkhead 104 and into reservoir 122. In other examples not depicted in FIG. 5A, pressure sensor 112 may be configured differently. For example, the deformable diaphragm may be welded flush with the surface of pressure sensor 112 such that housing ferrule 156 does not extend into reservoir 122. In this manner, housing ferrule 156 may reside within pressure sensor 112. In other examples, housing ferrule 156 may be recessed within pressure sensor 112 to provide an indent or cavity. According to these examples, bulkhead 104 and pressure sensor 112 in combination may provide a continuous surface that defines reservoir 122.

In addition to bulkhead 104 forming a portion of reservoir 122, bulkhead 104 may also support other components 120 of IMD 16. Components 120 may be mounted to or formed of bulkhead 104, and/or components 120 may reside within a space defined by bulkhead 126. For example, flexible circuit 114 may be coupled to pressure sensor 112 and a processor of IMD 16. Bulkhead space 126 may be defined by bulkhead 104, and may also be defined by top shield 116. Top shield 116 may mate with bulkhead 104 form a hermetic enclosure that protects components 120 within bulkhead space 126 from body tissues and fluids when IMD 16 is implanted within patient 12.

Together, top shield 116, bulkhead 104, and reservoir back housing 102 forms the exterior surface of IMD 16. In other examples, the exterior surface of IMD 16 may be formed by fewer components. For example, bulkhead 104 may reside completely within top shield 116. In other words, top shield 116 may mate to reservoir back housing 102 to create the exterior surface of IMD 16. Bulkhead 104 may then mount within top shield 116 or reservoir back housing 102.

Reservoir back housing 102, bulkhead 104, and top shield 116 may be constructed of biocompatible and/or corrosion-resistant materials because their surfaces come into contact with corrosive drugs, bodily fluids, or both. In some examples, the materials may only need to be non-corrosive and compatible with pharmacological agents, and not biological agents, to function within the example of FIG. 5A. Example materials include polymers, ceramics, composite materials, and metal alloys. Example metal alloys include stainless steel, aluminum alloys, and titanium alloys. Example titanium alloys include Grades 1, 2, 5, or 9 titanium. Although the same material may be used to form each of reservoir back housing 102, bulkhead 104, and top shield 116, different materials may also be used.

Although reservoir 122 is a reservoir for fluid as depicted in the example of FIG. 5A, pressure sensor 112 may be utilized to detect pressure in other types of fluid enclosures as well. For example the fluid enclosure may be a conduit that accommodates fluid from the refill port to the reservoir. In other examples, the fluid enclosure may be a conduit that accommodates fluid between the reservoir and the exit port of IMD 16. In this manner, pressure sensor 112 may form a portion of any fluid enclosure that retains or directs fluid within IMD 16. In an example where reservoir 122 is a conduit within bulkhead 104, all surrounding surfaces of bulkhead 104 that define at least a portion of the fluid enclosure may be considered a fluid enclosure wall, because bulkhead 104 defines at least a portion of a barrier defining the fluid enclosure.

Figure 5B:
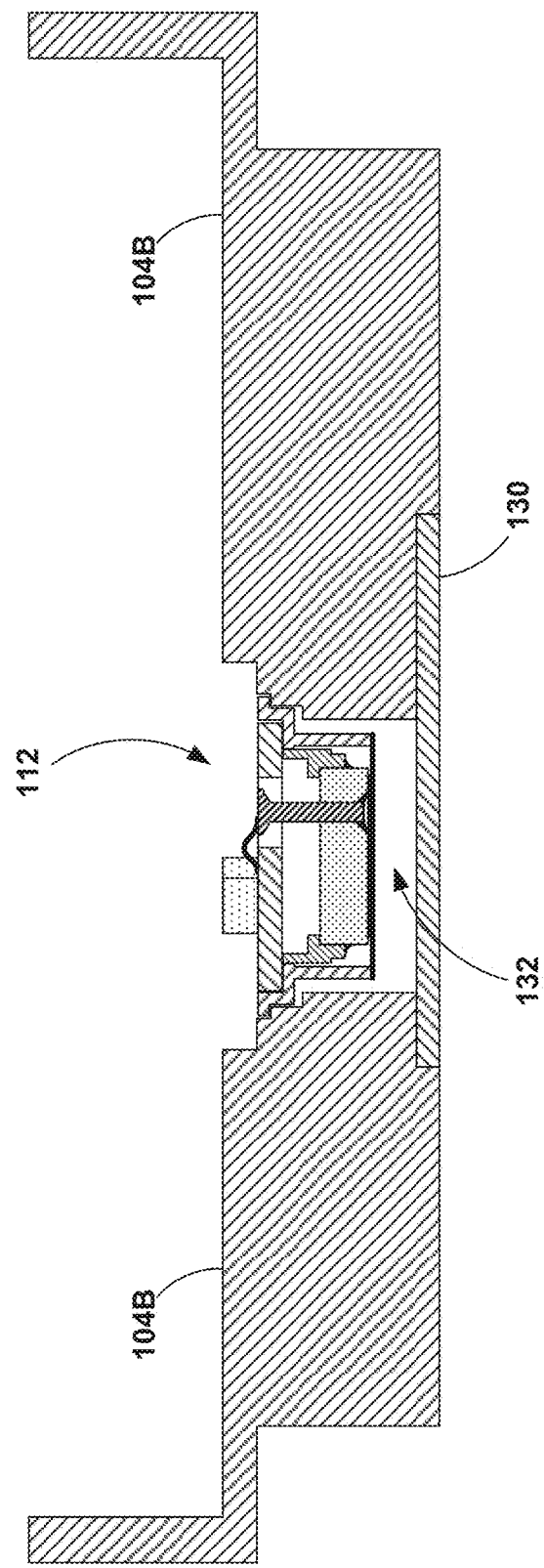
FIG. 5B is a conceptual diagram illustrating a cross-section of another example of an IMD that includes a fluid enclosure defined by a pressure sensor and a bulkhead of an IMD consistent with this disclosure.

FIG. 5B is a conceptual diagram illustrating a cross-section of example fluid channel 132 defined by pressure sensor 112 and bulkhead 104B. Fluid channel 132 is one example of a fluid enclosure. As shown in FIG. 5B, bulkhead 104B may provide a recessed mounting position for pressure sensor 112. Plate 130 may be attached to bulkhead 104B via one or more of a fastener, adhesive, weld, and/or any other attachment mechanism. Pressure sensor 112, plate 130, and bulkhead 104B may act as fluid enclosure walls that define fluid channel 132 within bulkhead 104B. In this manner, fluid channel 132 is one example of a fluid enclosure within bulkhead 104B that is capable of retaining fluid, or drug, inside IMD 16, for example. Fluid channel 132 may be a pathway that directs fluid from a reservoir to a pump mechanism, from a pump mechanism to an output port, or a refill port to a reservoir. As fluid is retained in or moves through fluid channel 132, pressure sensor 112 may detect the pressure of the fluid. This pressure may also be used to indicate the flow rate of the fluid.

Bulkhead 104B may separate a fluid reservoir (not shown in FIG. 5B) from electrical components housed within IMD 16. Bulkhead 104B may be similar to bulkhead 104A of FIG. 5A with the difference that bulkhead 104B does not directly expose pressure sensor 112 to fluid of the IMD 16 reservoir. The distance between pressure sensor 112 and plate 130 may generally be between approximately 0.1 mm and 10 mm. However, smaller or larger distances are also contemplated based upon the application in which pressure sensor 112 is intended. Smaller distances, and smaller volumes of fluid channel 132, may facilitate fluid flow functions while larger distances may facilitate fluid holding functions. In other examples, both bulkhead 104B and plate 130 may be manufactured from a single piece of material so that only bulkhead 104B and the external surface of pressure sensor 112 form the fluid enclosure walls of fluid channel 132.

Figure 6:
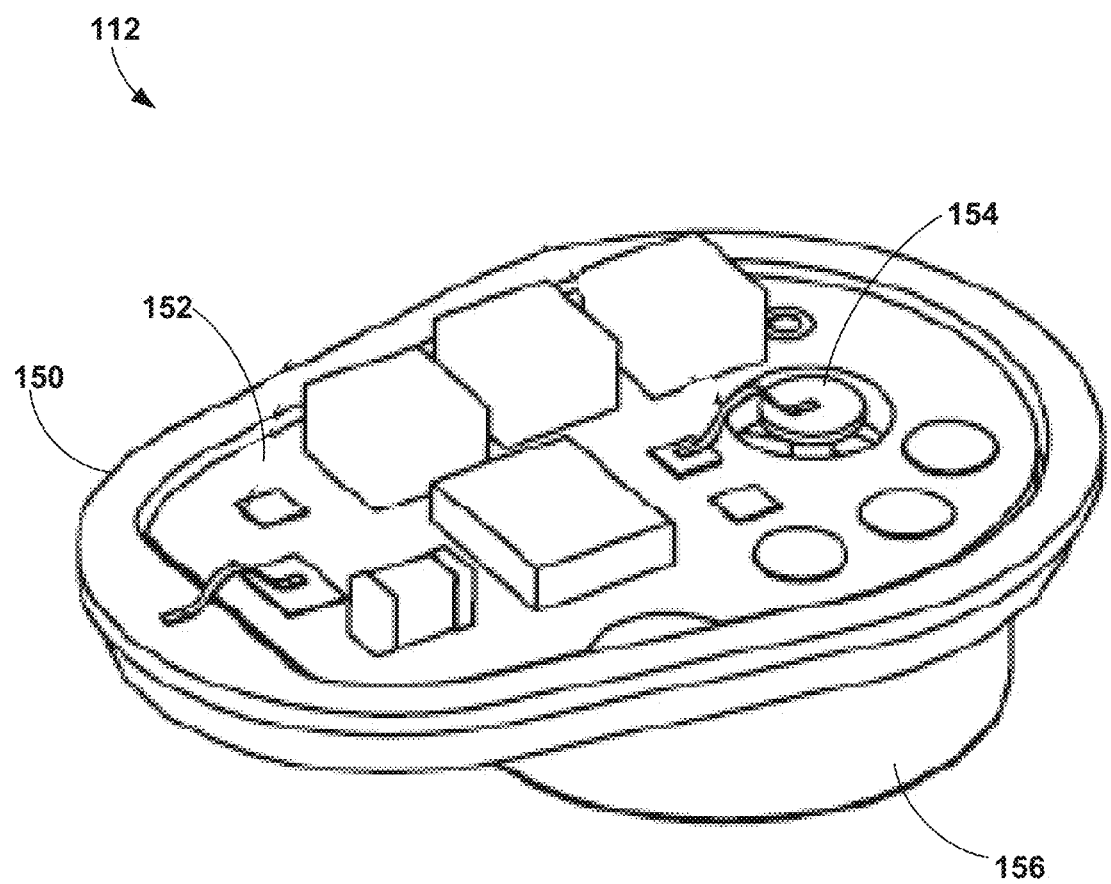
FIG. 6 is a conceptual diagram illustrating one example of a pressure sensor for use within an IMD consistent with this disclosure.

FIG. 6 is a conceptual diagram illustrating one example of a pressure sensor 112 for use within IMD 16. As shown in FIG. 6, pressure sensor 112 includes sensor housing 150, printed circuit board 152, and feedthrough pin 154. Housing ferrule 156 may be a portion of sensor housing 150 that extends with respect to the rest of sensor housing 150. Although housing ferrule 156 is cylindrical, other examples of pressure sensor 112 may provide a housing ferrule of other shapes such as a rectangle, square, and/or oval shape.

Sensor housing 150 may be shaped to self-align into an opening of bulkhead 104 sized and shaped to accept sensor housing 150. Although sensor housing 150 is eccentrically shaped in the example of FIG. 6, sensor housing 150 may instead be configured into any shape that allows pressure sensor 112 to self-align to a similarly shaped opening in bulkhead 104. An eccentric shape may generally be a non-circular shape. For example, a tear-drop shape or the shape of sensor housing 150 in FIG. 8 may be considered an eccentric shape. For the purposes of this disclosure, an eccentric shape is any structure that can only be matched to a similarly shaped opening in one position when rotated 360 degrees. These other shapes may include rounded shapes with notches or protrusions that "key" the orientation of pressure sensor 112 to bulkhead 104.

Printed circuit board 152 may also be shaped to fit within sensor housing 150. This shape of printed circuit board 152 may self-align the board within the housing. Printed circuit board 152 may also include circuitry or other components for the operation of pressure sensor 112. Printed circuit board 152 may also include an opening that enables electrical connection between printed circuit board 152 and other components of pressure sensor 112. For example, printed circuit board 152 may include an opening for feedthrough pin 154 to pass through from cylindrical housing ferrule 156.

Figure 7:
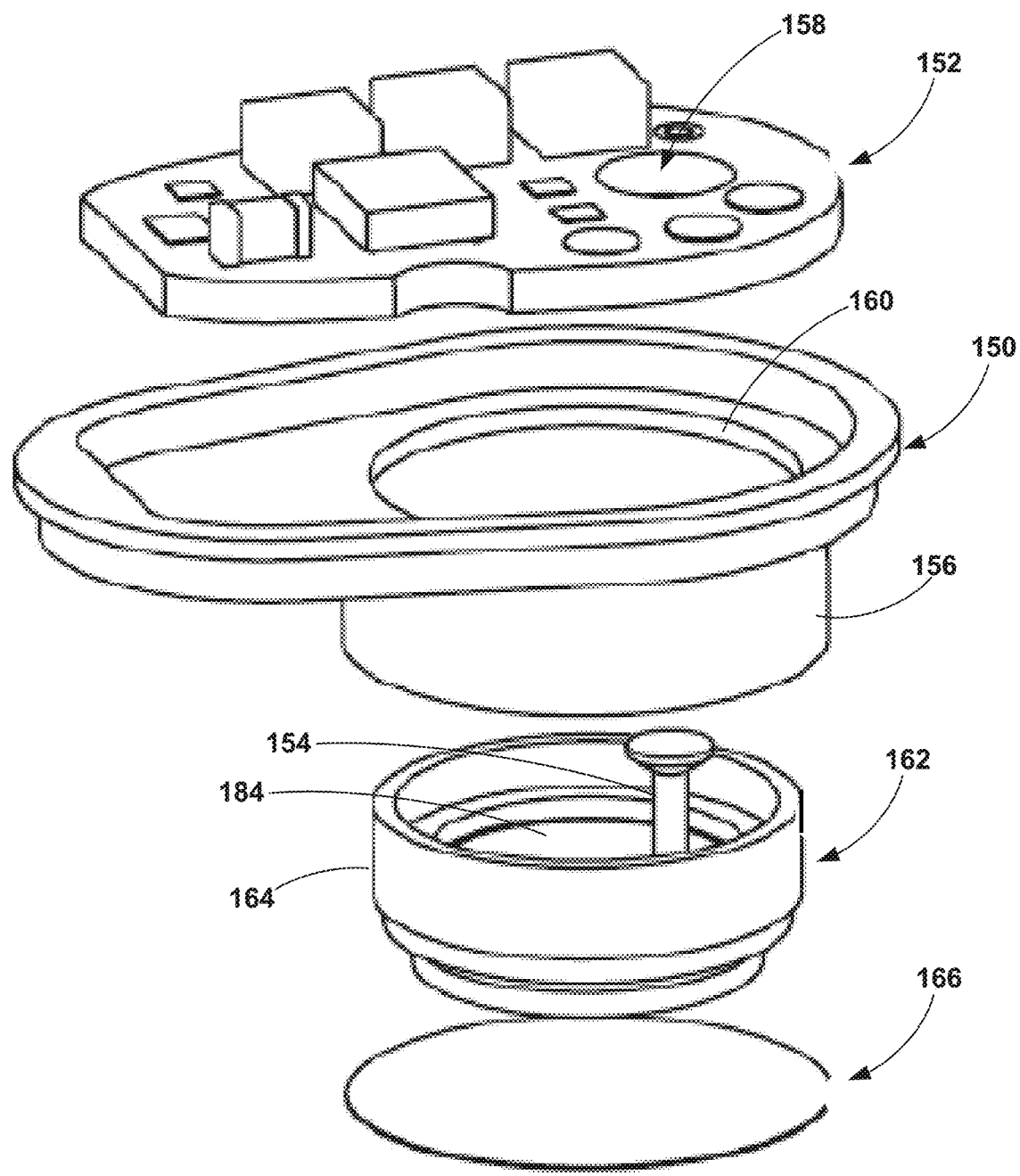
FIG. 7 is an exploded view of one example of a pressure sensor consistent with this disclosure.

FIG. 7 is an exploded view of pressure sensor 112 of FIG. 6. As shown in FIG. 7, components of pressure sensor 112 include printed circuit board 152, sensor housing 150, feedthrough assembly 162, and diaphragm 166. Some or all of these components may fit together to form the completed pressure sensor 112.

As discussed above, printed circuit board 152 may include one or more opening 158 sized and shaped to accept feedthrough pin 154. Opening 158 may be an aperture or other such void formed in printed circuit board 152. Printed circuit board 152 may be sized and shaped to fit within sensor housing 150. Sensor housing 160 may include housing ferrule 156 and one or more protrusions 160. The one or more protrusions 160 may provide a slightly smaller inner diameter than housing ferrule 156 in order to allow support structure 164 of feedthrough assembly 162 to tilt within housing ferrule 156. Support structure 164 may then be attached to protrusion 160, e.g., via welding or any other appropriate mechanism for securing support structure 164. The at least one protrusion 160 as depicted in FIG. 7 is an annular ring or lip, however, protrusion 160 may be a single protrusion or even a set of three or more protrusions circumferentially spaced within housing ferrule 156 and aligned in a plane substantially orthogonal to an axis of the cylindrical housing ferrule.

As shown in the example of FIG. 7, feedthrough assembly 162 includes support structure 164, rigid insulator 184, and feedthrough pin 154. Feedthrough pin 154 may be coupled to substantially rigid insulator 184 and may be electrically coupled to a capacitive plate (not shown) at a bottom surface of rigid insulator 184. Substantially rigid insulator 184 may be substantially rigid such that the capacitive plate (e.g. a metal coating at a bottom surface of substantially rigid insulator 184) defines a reference plane with respect to deflectable diaphragm 166. In this manner, substantially rigid insulator 184 may be capable of some elastic deformation without incurring plastic deformation or fracture. However, it may be desirable for substantially rigid insulator 184 to substantially maintain its shape under operating conditions of pressure sensor 112.

Rigid insulator 184 may be mounted to support structure 164, and support structure 164 may be positioned within housing ferrule 156. Support structure 164 may be secured in a desired position within housing ferrule 156 via one or more protrusions 160, e.g., by welding or otherwise securing support structure 164 to the one or more protrusions 160. Diaphragm 166 may be attached to a distal edge of housing ferrule 156. Diaphragm may function as a deformable capacitive plate for pressure sensor 112. Diaphragm 166 may be fixed along an entire edge to seal feedthrough assembly 162 within housing ferrule 156.

Figure 8:
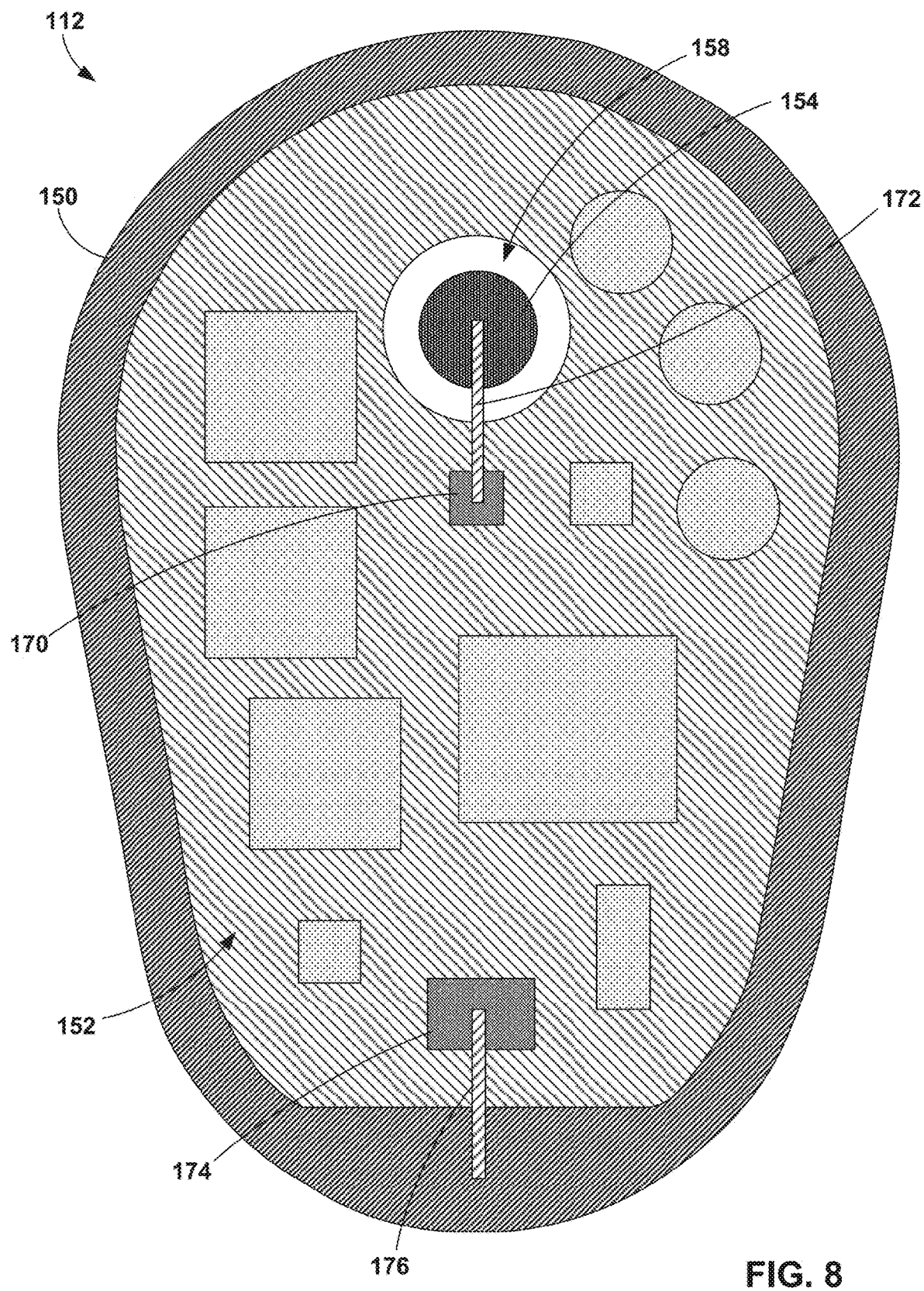
FIG. 8 is a conceptual diagram illustrating a top-down perspective view of one example of a pressure sensor consistent with this disclosure.

FIG. 8 is a conceptual diagram of a non-fluid contact side of one example of a pressure sensor 112. As shown in FIG. 8, pressure sensor 112 includes sensor housing 150, printed circuit board 152, feedthrough pin 154, conductive ribbons 172 and 176, and contacts 170 and 174. Sensor housing 150 may be configured in an eccentric shape to allow pressure sensor 112 to self-align to a similarly shaped opening in bulkhead 104. Sensor housing 150 may also provide a recessed support for printed circuit board 152 to be carried by sensor housing 150. Printed circuit board 152 may also be shaped for self alignment with respect to sensor housing 150.

Printed circuit board 152 may provide electrical contacts 170 and 174. Contacts 170 and 174 may provide connection points on printed circuit board 152 for conductive ribbons 172 and 176, respectively. Conductive ribbon 172 may electrically couples feedthrough pin 154 to contact 170. Also, conductive ribbon 176 may electrically couple sensor housing 150 to contact 174. Sensor housing 150 may conducts electrical energy between printed circuit board 152 and diaphragm 166 (of FIG. 7). Printed circuit board 152 may also provide an opening 158 configured to receive feedthrough pin 154.

Printed circuit board 152 may be configured in different shapes and sizes than those depicted in FIG. 8. In addition, multiple circuit boards may be housed within sensor housing 150. In some examples, two or more conductive ribbons may be used in place of one or both of conductive ribbons 172 and 176. Further, conductive ribbons 172 and 176 may be replaced with different conductive structures that electrically couple sensor housing 150 and feedthrough pin 154 to printed circuit board 152. For example, conductive traces may be formed in printed circuit board 152 that directly couple feedthrough pin 154 and sensor housing 150. In other examples, any other electrically conductive structure, such as a wirebond, may be utilized to electrically couple sensor housing 150 and feedthrough pin 154 to printed circuit board 152. Alternatively, a conductive epoxy may be used to secure printed circuit board 152 and provide electrical conductivity between printed circuit board 152 and sensor housing 150.

Figure 9:
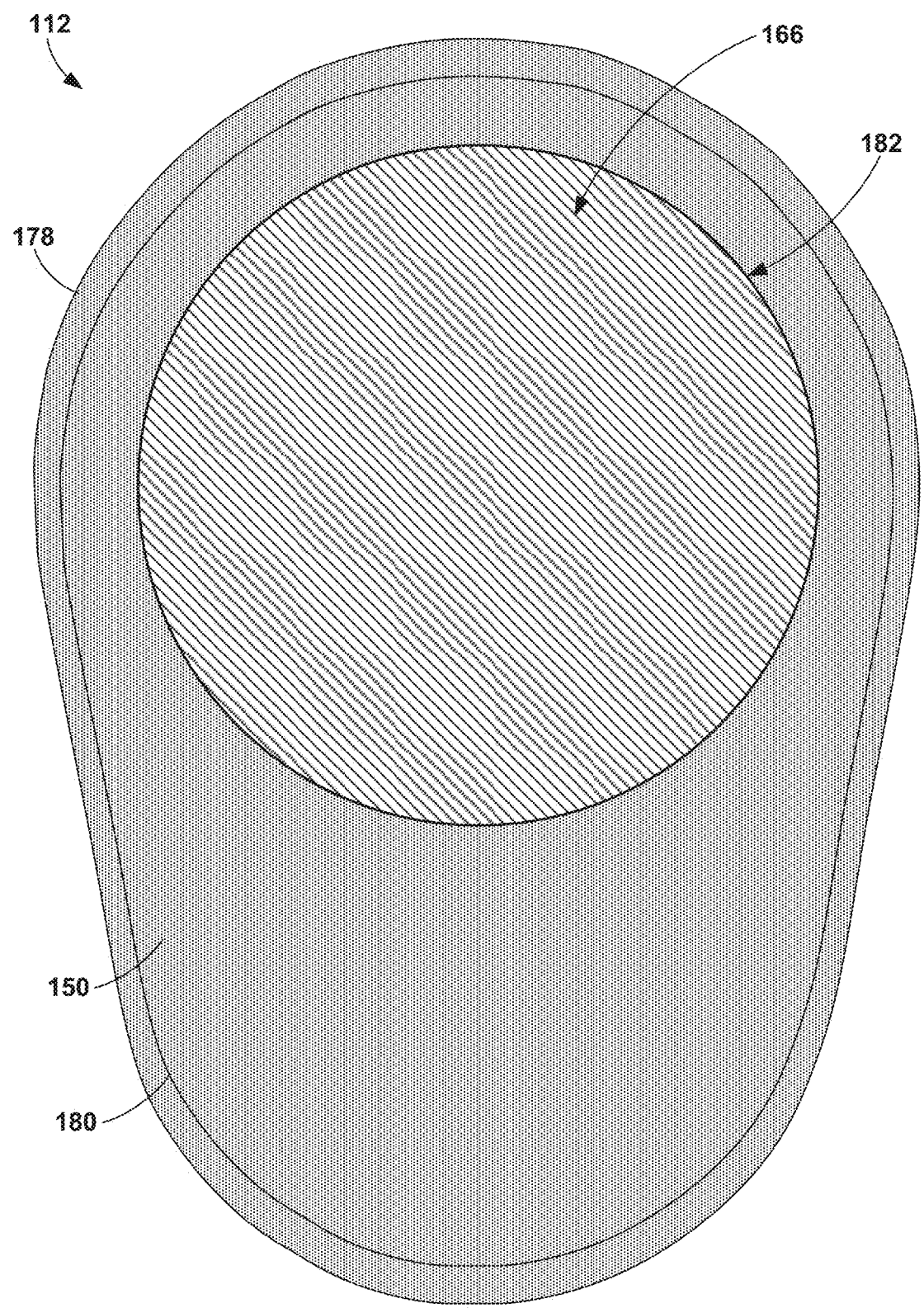
FIG. 9 is a conceptual diagram illustrating a bottom-up perspective view of one example of a pressure sensor including a diaphragm consistent with this disclosure.

FIG. 9 is a conceptual diagram illustrating a perspective view from an interior of a fluid enclosure of a fluid contacting side of a pressure sensor 112. As shown in FIG. 9, pressure sensor 112 includes sensor housing 150 and diaphragm 166. Sensor housing 150 may include an outer flange 178 and an inner edge 180. Outer flange 178 may provide a shelf or lip to contact, or reside adjacent to, bulkhead 104. When sensor housing 150 is placed within the opening of bulkhead 104, the outer edge of outer flange 178 may be sealed to bulkhead 104 with a laser seam weld or a different type of attachment or bonding method. In this manner, the top surface of outer flange 178 may be flush with bulkhead 104. In other examples, outer flange 178 may be larger than an opening in bulkhead 104 such that outer flange 178 prevents pressure 112 from passing through the opening in bulkhead 104. In some examples, inner edge 180 may contact a surface of bulkhead 104 to seal fluid within the fluid enclosure.

Diaphragm 166 is a deflectable capacitive plate of the capacitor used to measure pressure of fluid contacting diaphragm 166. Diaphragm 166 may be substantially annularly shaped and may completely cover an opening defined by housing ferrule 156 (not shown in FIG. 9). Diaphragm edge 182 may correspond to an outer surface of housing ferrule 156 to form a continuous outer surface of pressure sensor 112. Diaphragm 166 may be attached to housing ferrule 156 via welding, soldering, adhesives, or other attachment methods. In some examples, diaphragm edge 182 may not extend completely to the outer surface of housing ferrule 156. In other examples, diaphragm 166 may have a diameter larger than the outer diameter of housing ferrule 156 such that diaphragm edge 182 folds over housing ferrule 156.

Sensor housing 150 (including housing ferrule 156 not shown in FIG. 9) and diaphragm 166 may define an operative surface of pressure sensor 112. The operative surface contacts the fluid within the fluid enclosure partially defined by pressure sensor 112. In other examples, the operative surface may only include diaphragm 166. Although diaphragm 166 may be constructed as a solid structure or foil, diaphragm may be provided in other configurations. For example, diaphragm 166 may be constructed of multiple layers of the same material, layers of different materials, or sandwiched layers of different materials. For example, diaphragm 166 may be constructed of an insulating material sandwiched by two conductive foil layers.

Sensor housing 150 and diaphragm 166 may be constructed of biocompatible materials and/or anti-corrosive materials because their surfaces come into contact with corrosive drugs, bodily fluids, or both. In some examples, the materials may only need to be non-corrosive and compatible with pharmacological agents, and not biological agents, to function within the example of FIG. 9 or other examples herein. In addition, these materials may be electrically conductive. Example materials may include composite materials and metal alloys. Example metals or metal alloys may include aluminum, titanium, or nitinol. Example titanium alloys include Grades 1, 2, 5, or 9. The titanium alloy used to construct diaphragm 166 may be electrically conductive, flexible enough to deflect with increased pressure, able to resist plastic deformation or hysteresis, and able to resist cracking from cyclic deformation. Other materials that may be used alone or within an alloy may include gold, titanium, copper, niobium, nickel, aluminum, molybdenum, silver, or other such materials known in the art. A material used for diaphragm 166 may be manufactured with a thinness that allows the diaphragm to meet these performance requirements. Generally, the thickness of diaphragm 166 may be between 0.001 mm and 1.0 mm. More specifically, the thickness of diaphragm 166 may be between 0.02 mm and 0.13 mm. In one example, grade 9 titanium may be selected as the material for diaphragm 166. Although the same material may be used in diaphragm 166 and sensor housing 150, different materials may also be used. For example, different titanium alloys may be used.

Generally, a diameter of diaphragm 166 may be between approximately 3.0 millimeters (mm) and 20 mm. More specifically, the diameter of diaphragm 166 may be between 4.0 mm and 7.0 mm. In the example of FIG. 9, diaphragm 166 has a diameter of approximately 5.6 mm. A length of pressure sensor 112 may be generally between 5.0 mm and 30 mm, and the width of pressure sensor 112 may be generally between 3.5 mm and 22 mm. In the example of FIG. 9, the length and width of pressure sensor 112 may be approximately 10 mm and 7 mm, respectively. In other examples, pressure sensor 112 may be constructed of smaller or large dimensions, depending upon the desired application of pressure sensor 112.

Figure 10:
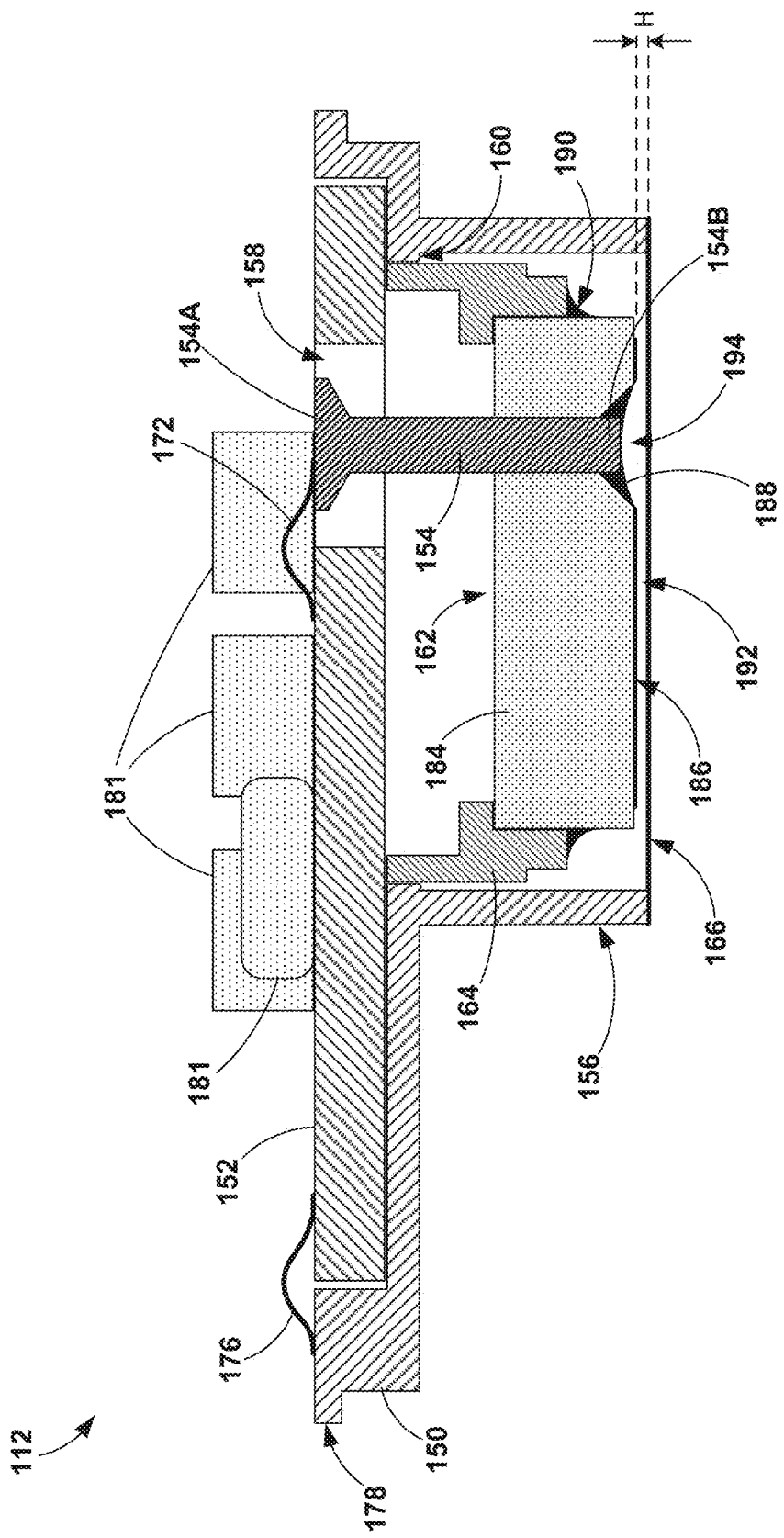
FIG. 10 is a conceptual diagram illustrating a cross-section of one example of a pressure sensor consistent with this disclosure.

FIG. 10 is a conceptual diagram illustrating a cross-section perspective view of pressure sensor 112. As shown in the example of FIG. 10, pressure sensor 112 includes sensor housing 150, printed circuit board 152, electrical components 181, conductive ribbons 172 and 176, feedthrough pin 154, support structure 164, rigid insulator 184, rigid capacitive plate 186, diaphragm 166, oil cup 188, and insulator bond 190. When assembled, diaphragm 166 and rigid capacitive plate 186 may form a capacitor that pressure sensor 112 utilizes to detect changes in capacitance caused by fluid pressure against diaphragm 166.

According to the example of FIG. 10, sensor housing 150 includes outer flange 178, housing ferrule 156, and at least one protrusion 160. Sensor housing may also include a recessed support that accepts and secures a printed circuit board 162 or other circuitry of pressure sensor 112. Although there may be a gap between sensor housing 150 and the edge of printed circuit board 152, some examples may not provide for any gap between the two structures. Outer flange 178 may be larger than the opening in bulkhead 104 to enable pressure sensor 112 to mate against bulkhead 104. In the example of FIG. 10, outer flange 178 is shown around a circumference of sensor housing 150, but in other examples outer flange 178 may consist of one or more protrusions from sensor housing 150.

As depicted in the example of FIG. 10, housing ferrule 156 is a portion of sensor housing 150 that surrounds and protects feedthrough assembly 162. Housing ferrule 156 is cylindrical in shape, but housing ferrule 156 may be constructed in other shapes as well. As depicted in the example of FIG. 10, housing ferrule 156 has openings at both ends and provides a mounting surface for diaphragm 166 at one end. In addition, at least one protrusion 160 provides a mounting point, or an attachment surface, for support structure 164 of feedthrough assembly 162 to be secured within housing ferrule 156. The at least one protrusion 160 may define a smaller inner diameter than housing ferrule 156, where the larger inner diameter of housing ferrule 156 allows feedthrough assembly 162 to be tilted to orient rigid capacitive plate 186 into a desired position.

The at least one protrusion 160 may be provided as an annular ring, a lip, a single protrusion, or even a set of three or more protrusions circumferentially spaced within housing ferrule 156 and aligned in a plane substantially orthogonal to an axis of cylindrical housing ferrule 156. The at least one protrusion 160 may be integrally formed with housing ferrule 156. In other examples, support structure 164 may instead provide the functional equivalent of protrusion 160 (e.g., one or more protrusions on an outer surface of support structure 164) to mate with an inner surface of housing ferrule 156. The at least one protrusion 160 may be integrally formed with support structure 164. In alternative examples, the at least one protrusion 160 may be a separate structure configured to be attached to support structure 164 and an inner surface of housing ferrule 156.

Printed circuit board 152 may be inset within sensor housing 150. Printed circuit board 152 may carry circuitry used for operation of pressure sensor 112. Printed circuit board 152 may also include other electrical components 181. Although, according to the example of FIG. 10, electrical components 181 are shown extending from printed circuit board 152, electrical components 181 may be recessed within printed circuit board 152. In addition, opening 158 may formed in printed circuit board 152. Opening 158 may allow nailhead 154A of feedthrough pin 154 to extend to or above a surface of printed circuit board 152 for connection to, for example conductive ribbon 172. Nailhead 154A may be provided as an attachment point for conductive ribbon 172. Nailhead 154A may include an attachment surface having a larger diameter than the shaft of feedthrough pin 154. This attachment surface may also be configured to facilitate electrical coupling with conductive ribbon 172. Sensor housing 150 may conduct electrical current between diaphragm 166 and printed circuit board 152 via conductive ribbon 176. In other examples, a conductive epoxy or other electrical conductive connections may be used instead of conductive ribbon 176.

Feedthrough assembly 162 may be configured to be disposed within housing ferrule 156. As shown in the example of FIG. 10, feedthrough assembly 162 includes support structure 164, substantially rigid insulator 184, feedthrough pin 154, rigid capacitive plate 186, oil cup 188, and insulator bond 190. Substantially rigid insulator 184 may be non-conductive and may provide a support for capacitive plate 186. By not conducting electricity, substantially rigid insulator 184 may electrically isolates capacitive plate 186 from any other electrically conductive surface that may cause an undesirable short circuit. Rigid insulator 184 may be substantially rigid and generally inflexible to retain its shape within pressure sensor 112, but rigid insulator 184 may be capable of deforming to some degree. However, rigid insulator 184 may be configured not to deform during normal operation of pressure sensor 112 to maintain the metal coating in a reference plane with respect to deflectable diaphragm 166. Substantially rigid insulator 184 is shown in a cylindrical shape according to the example of FIG. 10, but the insulator may be formed into other shapes as long as it provides a suitable surface for capacitive plate 186. Materials suitable for substantially rigid insulator may include ceramics, composite materials, polymers, or other electrically insulative materials.

According to the example of FIG. 10, capacitive plate 186 is disposed on substantially rigid insulator 184 and may be a metal alloy bonded directly to substantially rigid insulator 184. In one example, capacitive plate 186 is a gold braze that is directly bonded to substantially rigid insulator 104. In other examples, capacitive plate 186 may be constructed by sputter coating, ion beam coating, chemical vapor deposition, using an adhesive to join the metal alloy with substantially rigid insulator 184, or any other method known in the art. Capacitive plate 186 may also be constructed with layers of one or more different metals. Example metals or metal alloys that may be used to construct capacitive plate 186 may include gold, titanium, copper, niobium, nickel, aluminum, molybdenum, silver, or any other such materials known in the art. Although capacitive plate 186 does not cover the entire surface of substantially rigid insulator 184 as shown in the example of FIG. 10, capacitive plate 186 may cover the entire insulator in other examples. Capacitive plate 186 may or may not be configured to be rigid by itself. In some examples capacitive plate 186 may be arranged in a rigid position with respect to deflectable diaphragm based on rigidity provided by substantially rigid insulator 184.

Capacitive plate 186 may be electrically coupled to pin end 154B of feedthrough pin 154. Capacitive plate 186 may fill a depression 194 of rigid insulator 184 to create an oil cup 188. Oil cup 188 may be a collection of the same or similar material used to form capacitive plate 186. When oil cup 188 is formed around pin end 154B, the metal alloy of rigid capacitive plate 186 may bond to pin end 154B of feedthrough pin 154. Since feedthrough pin 154 terminates at pin end 154B within depression 194 of rigid insulator 184, feedthrough pin 154 is recessed from the capacitive surface of rigid capacitive plate 186. Therefore, the possibility that feedthrough pin 154 could cause a short circuit between capacitive plate 186 and diaphragm 166 by capacitive plate 186 being closer to diaphragm 166 than desired may be minimized. Alternatively, a different conductive material than used to form capacitive plate 186 may be used to create oil cup 188 and couple rigid capacitive plate 186 and feedthrough pin 154.

Feedthrough pin 154 may be set away from a center axis of rigid insulator 184 to minimize an impact of depression 194 on measured capacitance between diaphragm 166 and capacitive plate 186. In this manner, the center axis of feedthrough pin 154 may not be shared with the center axis of rigid insulator 184. In addition, an offset position of feedthrough pin 154 may allow the use of different printed circuit boards with layouts accommodated by the ability to move the location of feedthrough pin by simply rotating feedthrough assembly 162 with respect to housing ferrule 156. However, feedthrough pin 154 may be located at any radial or circumferential position as long as feedthrough pin 154 does not contact a conductive surface other than rigid capacitive plate 186. Feedthrough pin 154 may be specifically configured to pass electrical current from rigid capacitive plate 186, through rigid insulator 184, and to printed circuit board 152 without contacting other conductive surfaces.

Rigid insulator 184 may be held in place by support structure 164. Support structure 164 may be a cylindrical collar that mounts rigid insulator 184 to sensor housing 150. In other examples, support structure 184 may be comprised of multiple separate braces that mount rigid insulator 184 to sensor housing 150. Rigid insulator 184 may be attached to support structure 164 with insulator bond 190. Insulator bond 190 may be an adhesive or melted alloy that is deposited around an outside edge of rigid insulator 184 to bond rigid insulator 184 to support structure 164. In other examples, rigid insulator 184 may be attached to support structure 164 with pins, clamps, snap enclosures, pressure fit, or any other mechanical method to secure rigid insulator 184.

Support structure 164 may be attached to sensor housing 150 via at least one protrusion 160. The at least one protrusion 160 may extend from an inner surface of housing ferrule 156 to contact an outer edge of support structure 164. Support structure 164 may be welded or otherwise secured to the at least one protrusion 160. The at least one protrusion 160 may allow feedthrough assembly 162 to tilt within housing ferrule 156 to orient rigid capacitive plate 186 in a desired plane with respect to diaphragm 166. Generally, the at least one protrusion 160 comprises less than 20 percent of a length of housing ferrule 156 between the distal end and the proximal end of housing ferrule 156, but the at least one protrusion 160 may have any height that still allows for the tilting of feedthrough assembly 162. Once support structure 164 is secured in place, rigid capacitive plate 186 may be secured such that it does not move relative to sensor housing 150.

Diaphragm 166 may operate as the second capacitive plate of capacitive pressure sensor 114. Diaphragm 166 may be attached to the distal edge of housing ferrule 156. Diaphragm 166 may be welded or soldered to housing ferrule 156. In other examples, diaphragm 166 may be adhered or bonded to housing ferrule 156. Since diaphragm 166 is deflectable, or displays elastic deformation, diaphragm 166 may provide one or more indications of changing fluid pressure. When assembled, pressure sensor 112 may define a height "H" of a capacitive gap 192 between rigid capacitive plate 186 and diaphragm 166 when no fluid pressure is exerted upon diaphragm 166. Capacitive gap 192 may also be referred to as a pick-off gap as known in the relevant arts. Generally, H is between approximately 0.01 mm and 0.25 mm. In the example of FIG. 10, H is approximately 0.08 mm. When the pressure increases against diaphragm 166, H will decrease accordingly. Although the gas filling capacitive gap 192 may be air, other inert or non-combustible gases may be used to fill this space within pressure sensor 112. Alternatively, capacitive gap 192 may be a vacuum.

Figure 11:
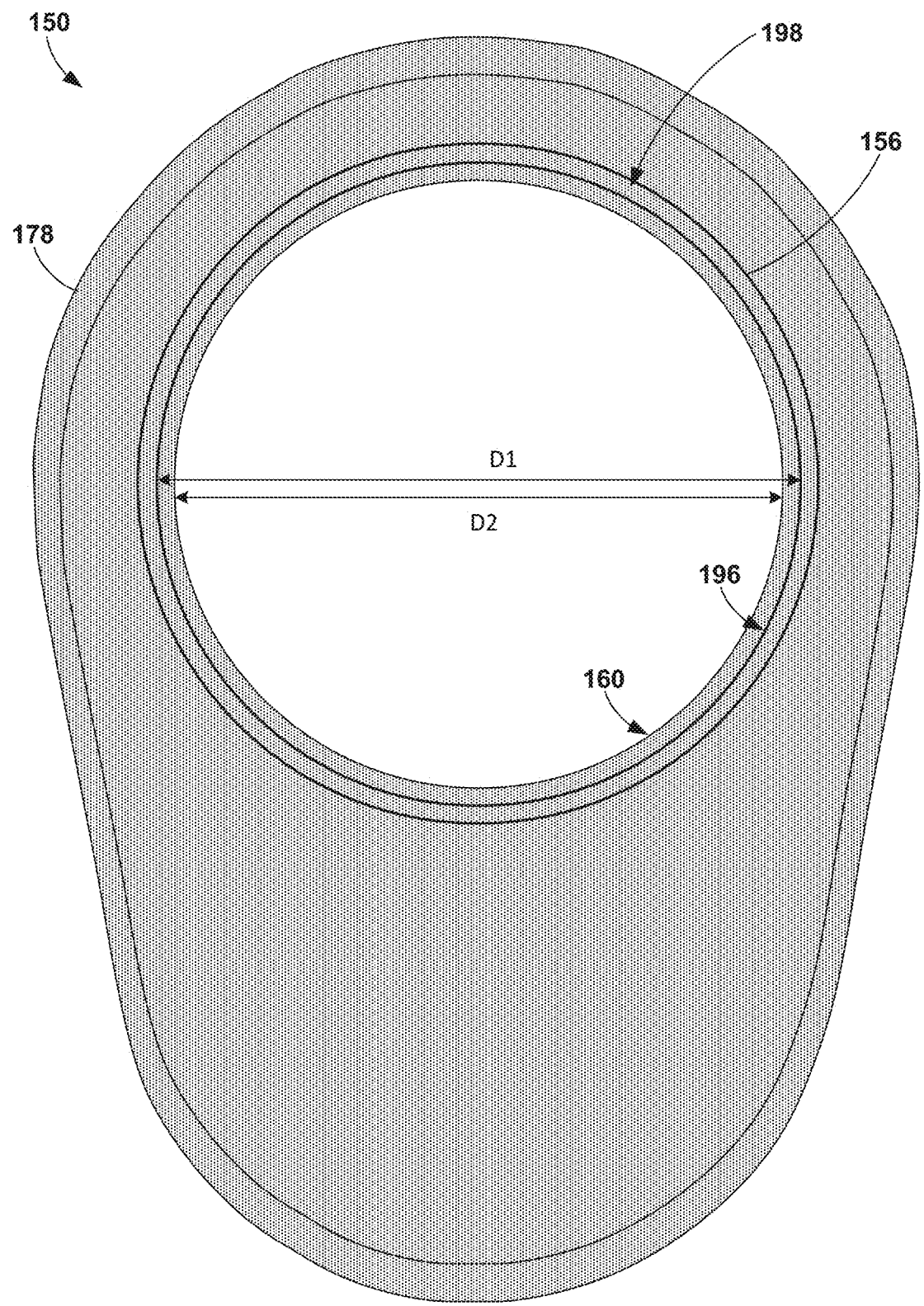
FIG. 11 is a conceptual diagram illustrating one example of a main housing of a pressure sensor that includes a housing ferrule consistent with this disclosure.

FIG. 11 is a conceptual diagram illustrating the sensor housing 150 and an inside of housing ferrule 156. As shown in FIG. 11, sensor housing 150 includes housing ferrule 156, at least one protrusion 160, and outer flange 178. Housing ferrule 156 includes an outer edge 198 that provides an attachment spot for diaphragm 166 (not shown). Housing ferrule 156 also has an inner surface 196 that defines inner diameter D1. At least one protrusion 160 extends inward from housing ferrule 156 to define an inner diameter D2. D1 is larger than D2 so that feedthrough assembly 162 can be tilted within housing ferrule 156, but the at least one protrusion 160 is still close enough to support structure 164 for attachment to protrusion 160.

Generally, D1 may be between approximately 2.8 mm and 19 mm. More specifically, D1 may be between approximately 3.9 mm and 6.9 mm. In the example of FIG. 9, D1 is approximately 5.0 mm. D1 may also be generally 0.1 mm to 10.0 mm larger than D2 in the example of FIG. 9. In other words, the width of protrusion 160 is generally between 0.05 mm to 2.0 mm. In the example of FIG. 9, D2 is approximately 4.6 mm. In other examples, D1 and D2 may be of smaller or larger dimensions, depending upon requirements for positioning of feedthrough assembly 162.

In alternative examples, the at least one protrusion 160 may be constructed as a part of support structure 164 instead of housing ferrule 156. Therefore, housing ferrule 156 may have a single inner diameter and support structure 164 provides one or more attachment points that allow feedthrough assembly 162 to tilt within housing ferrule 156 when orienting capacitive plate 186. For example, the at least one protrusion 160 may take the form of an annular ring on the outside of support structure 164. In any case, according to this example, feedthrough assembly 162 is provided the necessary space to define the desired capacitive gap 192 between diaphragm 166 and rigid capacitive plate 186.

Figure 12:
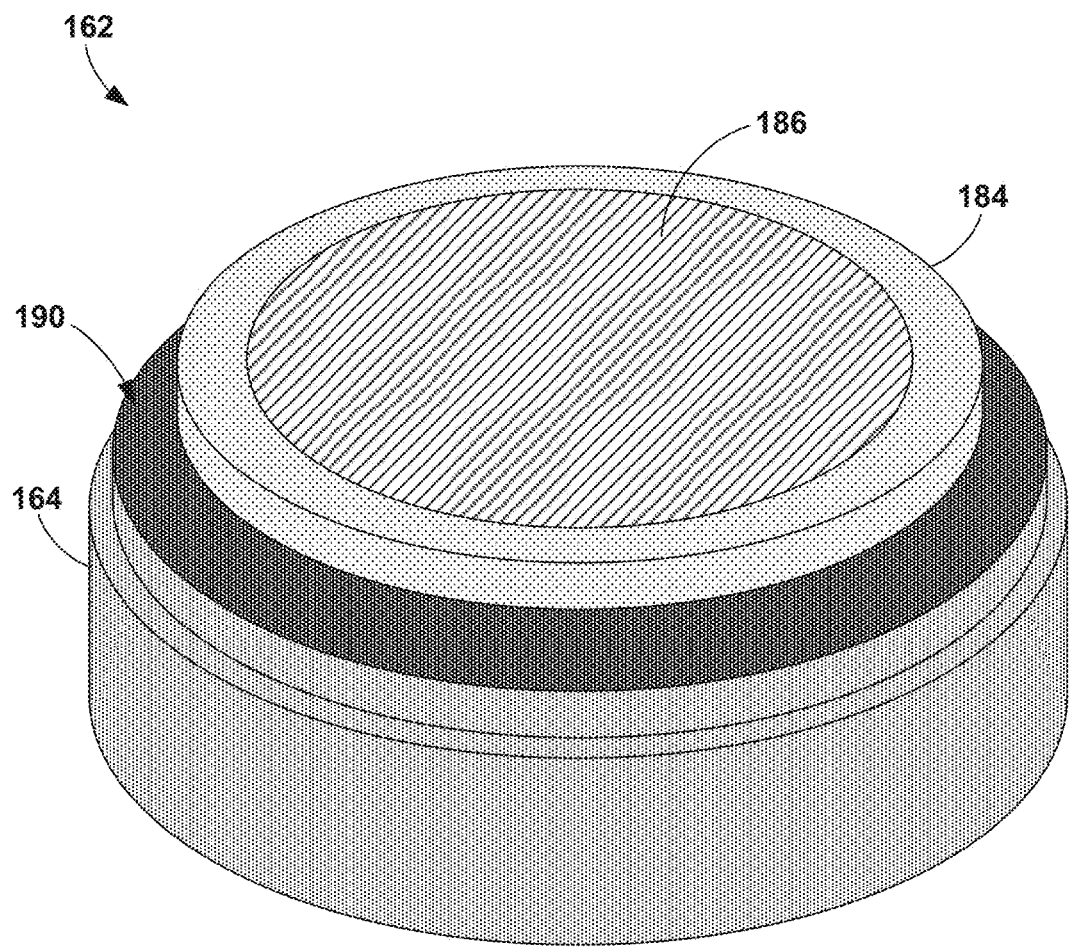
FIG. 12 is a conceptual diagram illustrating one example of a feedthrough assembly and a metal coating capacitive plate consistent with this disclosure.

FIG. 12 is a perspective diagram showing a perspective view of the capacitive plate side of feedthrough assembly 162. As shown in FIG. 12, feedthrough assembly 162 includes support structure 164, rigid insulator 184, capacitive plate 186, and insulator bond 190. Support structure 164 is bonded to rigid insulator 184 with insulator bond 190 around the entire circumference of rigid insulator 184. Insulator bond 190 may be formed in a manner in which the material settles down between rigid insulator 184 and an inner surface of support structure 164 to secure the components together. Insulator bond 190 may be formed by placing rigid insulator 184 within support structure 164 and positioning a ring of material, e.g., gold, silver, copper, molybdenum, or other material known in the art, around rigid insulator 184 and above support structure 164. Feedthrough assembly 162 is then heated until the material melts and flows down between rigid insulator 184 and support structure 164. This settling and forming of insulator bond 190 may shift or raise rigid insulator 184 from support structure 164. In this manner, rigid insulator 184 may be secured in a plane no longer parallel to the plane formed by support structure 164.

Capacitive plate 186 is deposited on the surface of rigid insulator 184. As shown in the example of FIG. 12, capacitive plate 186 may be a metal alloy that does not cover the entire surface of rigid insulator 184. This smaller diameter of rigid capacitive plate 186 may prevent any electrical interference between rigid capacitive plate 186 and insulator bond 190. Although capacitive plate 186 may have a uniform thickness, some variation in a thickness of the deposited metal alloy may be present due to manufacturing process variations. However, an effect caused by any non-uniformities in capacitive plate 186 may be minimized due to the assembly process for pressure sensor 112 described herein.

Figure 13:
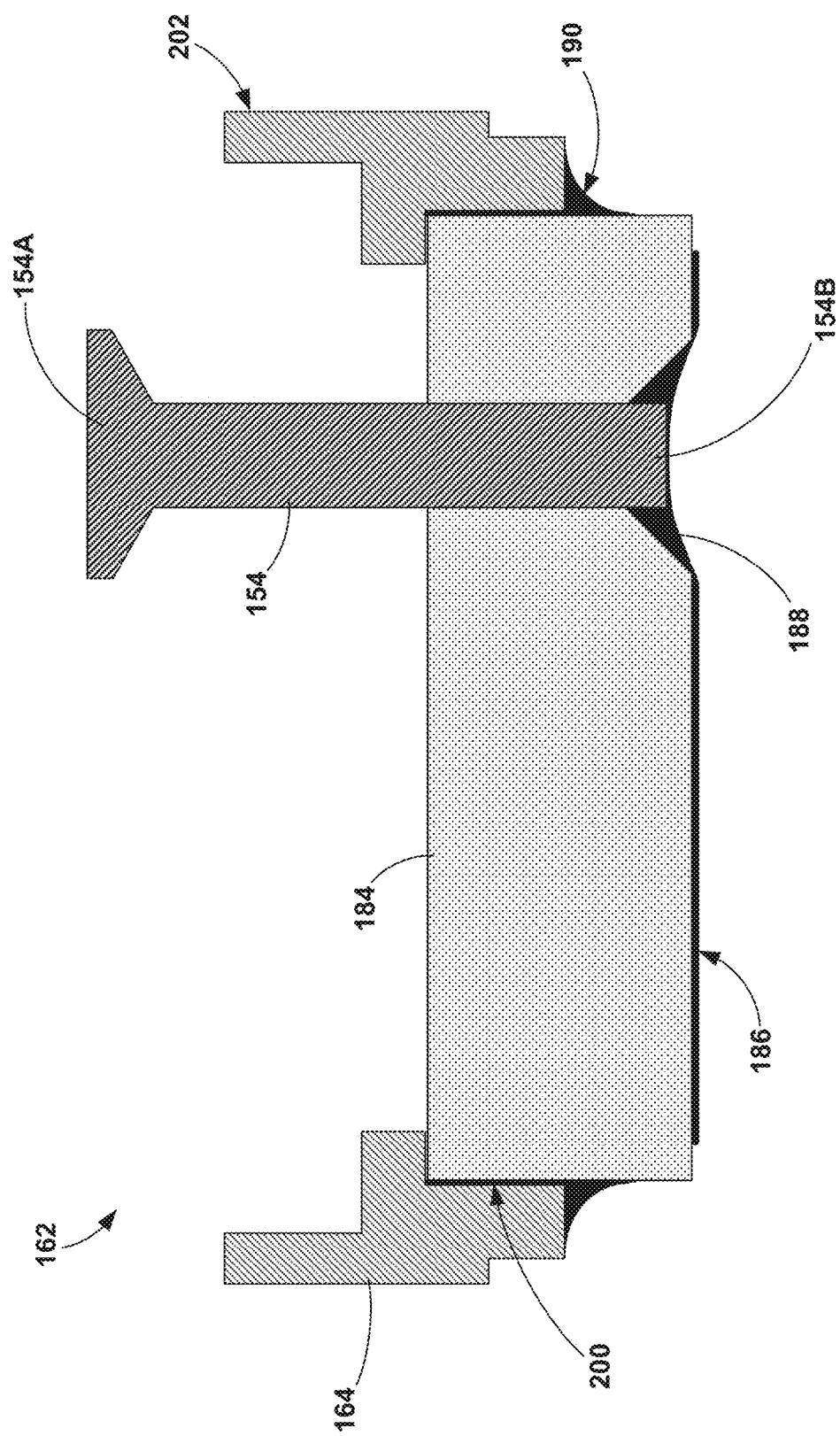
FIG. 13 is a conceptual diagram illustrating a cross-section of a feedthrough assembly consistent with this disclosure.

FIG. 13 illustrates a perspective view of a cross-section of feedthrough assembly 162. Similar to example shown in FIG. 10, FIG. 13 shows that feedthrough assembly 162 includes feedthrough pin 154, support structure 164, rigid insulator 184, rigid capacitive plate 186, diaphragm 166, oil cup 188, and insulator bond 190. In addition, FIG. 13 shows bond layer 200 and proximal end 202 of support structure 164. Proximal end 202 of support structure 164 may be used to mount feedthrough assembly 162 to sensor housing 150. More specifically, proximal end 202 may be welded directly to at least one protrusion 160 inside of housing ferrule 156.

Bond layer 200 may be a layer or film created between support structure 164 and rigid insulator 184. Bond layer 200 may be formed by directly placing the adhesive or material between these structures. Alternatively, bond layer 200 may be formed when the amorphous material is applied to create insulator bond 190 and a portion of the material fills a gap between support structure 164 and rigid insulator 184. During manufacturing, bond layer 200 may cause rigid insulator 104 to be displaced from the surfaces of support structure 164 so that rigid capacitive plate 186 is no longer square with support structure 164. This tilting or slanting of rigid insulator 184 may be substantially negligible when pressure sensor 112 is assembled according to techniques described herein. For example, at least one protrusion 160 may allow support structure 164 to be tilted within housing ferrule 156 to orient capacitive plate 186 to a desired plane substantially parallel to a plane of diaphragm 166.

Figure 14:
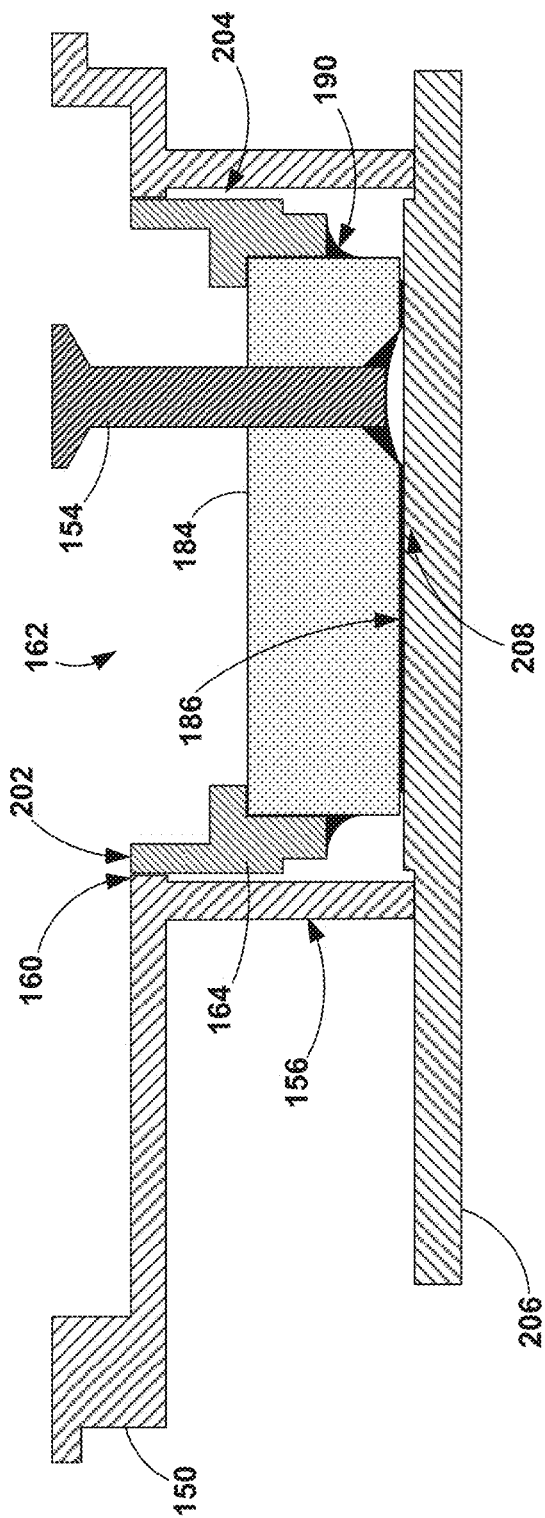
FIG. 14 is a conceptual diagram illustrating one example of an assembly tool that may be used to set a capacitive gap of a pressure sensor consistent with this disclosure.

FIG. 14 is a conceptual diagram illustrating an assembly tool 210 that may be used to define a capacitive gap between capacitive plate 186 and diaphragm 166. As shown in FIG. 14, assembly tool 210 includes base plate 206 and stage 208 raised from base plate 206. A height of stage 208 above a top surface of base plate 206 may be equivalent to a capacitive gap 192 created between the two capacitive plates of the capacitor. In this manner, stage 208 may define a plane parallel to the plane of base plate 206 so that capacitive gap 192 is substantially uniform.

Housing ferrule 156 of sensor housing 150 may be placed around stage 208 such that a distal edge of housing ferrule 156 contacts a top surface of base plate 206. The distal edge of housing ferrule 156 may be an edge furthest from the rest of sensor housing 150. Feedthrough assembly 162 may be placed within housing ferrule 156 such that that capacitive plate 186 contacts stage 208. Capacitive plate 186 may contact stage 208 such that it is substantially flush with stage 208. By contacting stage 208, capacitive plate 186 may be oriented in a plane substantially parallel to a plane created by the distal edge of housing ferrule 156. Feedthrough assembly 162 may also be circumferentially oriented to position feedthrough pin 154 appropriately within pressure sensor 112.

In some cases, feedthrough assembly 162 may need to be tilted within housing ferrule 156 to properly seat capacitive plate 186 to stage 208. In one example, rigid insulator 184 may have been lifted or offset slightly from support structure 164. In another example, capacitive plate 186 may have varying thickness across the plate due to manufacturing defects. Ferrule gap 204 is provided to enable this tilting to occur while allowing proximal end 202 of support structure 164 to contact the at least one protrusion 160 for attachment to sensor housing 150. Upon removal of assembly tool 210, diaphragm 166 may be attached, e.g., welded, to the distal edge of housing ferrule 156.

Stage 208 as shown in FIG. 14 is generally cylindrical in shape, but stage 208 may be configured in any shape that fits within housing ferrule 156 and creates a plane. In other examples, stage 208 may be comprised of three or more separate protrusions from base plate 206 that form a plane parallel to the top surface of base plate 206. The height of stage 208 from the top surface of base plate 206 may be generally between 0.01 mm and 0.25 mm. In the example of FIG. 14, stage 208 may have a height of approximately 0.08 mm.

Figure 15:
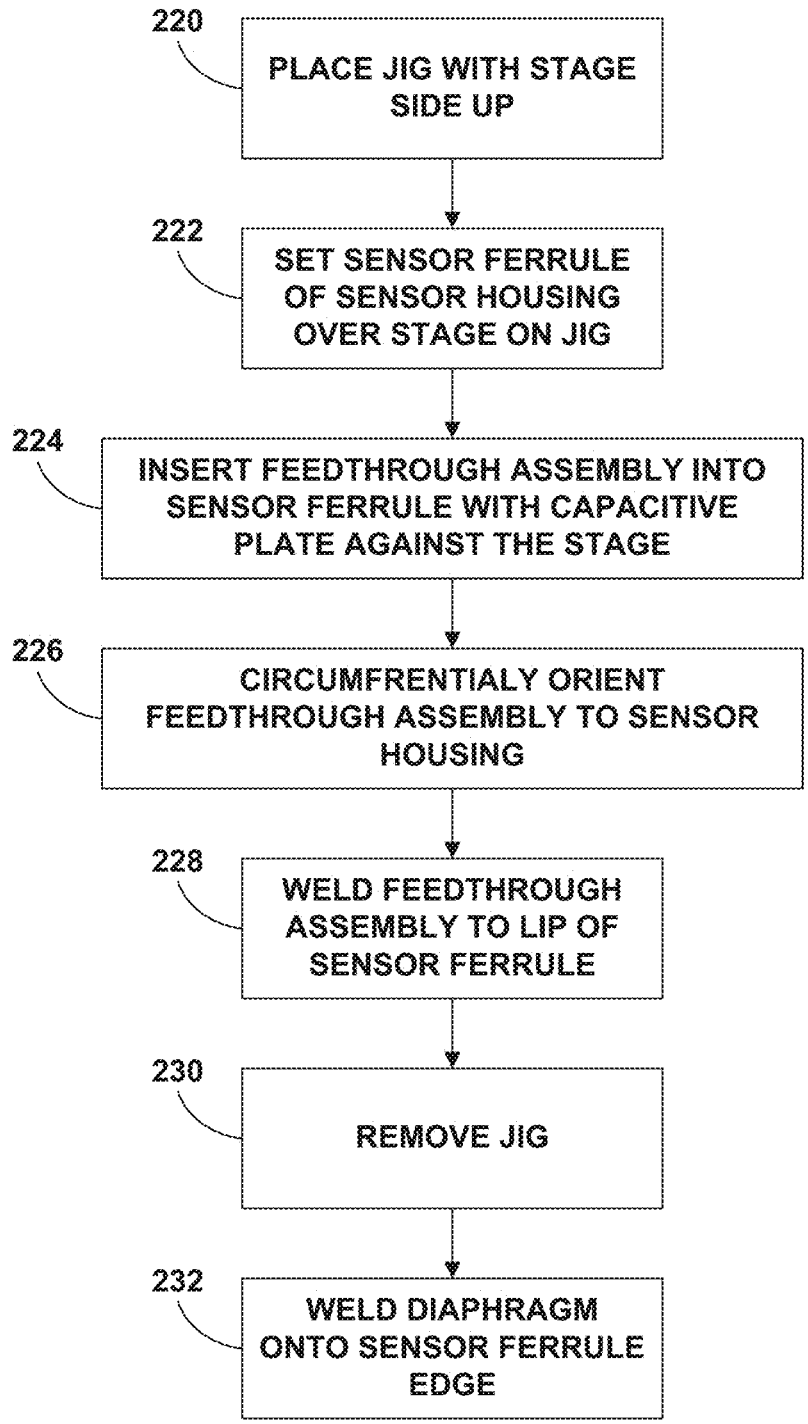
FIG. 15 is a flow diagram illustrating one example of a method for mounting a feedthrough assembly of a pressure sensor consistent with this disclosure

FIG. 15 is a flow diagram describing an example method for mounting feedthrough assembly 162 within pressure sensor 112 and attaching diaphragm 166. As shown in FIG. 15, assembly tool 210 is placed on a surface with stage 208 facing upwards (220). Next, housing ferrule 156 of sensor housing 150 is set over stage 208 such that the distal edge of housing ferrule 156 contacts the top surface of base plate 206 (222).

Feedthrough assembly 162 is then inserted into housing ferrule 156 so that rigid capacitive plate 186 contacts stage 208 (224). This seating process may also involve pressing rigid capacitive plate 186 against stage 208. Feedthrough assembly 162 is then circumferentially oriented to sensor housing 150 to allow feedthrough pin 154 to pass through opening 158 in printed circuit board 152 (226). Once oriented, support structure 164 of feedthrough assembly 162 is welded to protrusion 160 of housing ferrule 156 (228). Assembly tool 210 is then removed from housing ferrule 156 (230) and diaphragm 166 is welded into the distal edge of housing ferrule 156 (232).

Figure 16:
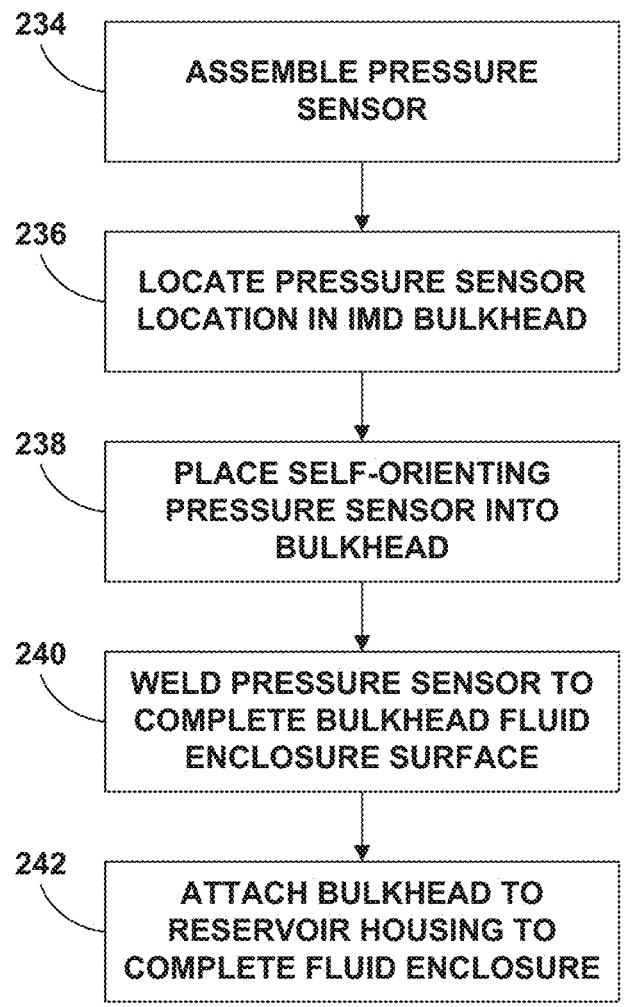
FIG. 16 is a flow diagram illustrating one example of a method for orienting a pressure sensor within an IMD consistent with this disclosure.

FIG. 16 is a flow diagram illustrating an example technique for orienting pressure sensor 112 within bulkhead 104 of IMD 16. As shown in FIG. 16, pressure sensor 112 is first assembled according, for example, the method of FIG. 15 (234). Once assembled, the opening for pressure sensor 112 is located in bulkhead 104 (236). Pressure sensor 112 is then placed into the opening of bulkhead 104 (238). Since pressure sensor 112 is configured as a shape that is self-aligning to the opening, there is only one way that pressure sensor 112 will fit within the opening of bulkhead 104.

Once pressure sensor 112 is in place, sensor housing 150 of pressure sensor 112 is welded into bulkhead 104 to further define the fluid enclosure (240). Next, bulkhead 104 is attached (e.g., welded) to reservoir back housing 102 to complete the fluid enclosure (242). Additional pressure sensors 112, such as a pressure sensor near refill port 28, may be added to bulkhead 104 or other fluid enclosures in the same self-aligning manner.

Figure 17:
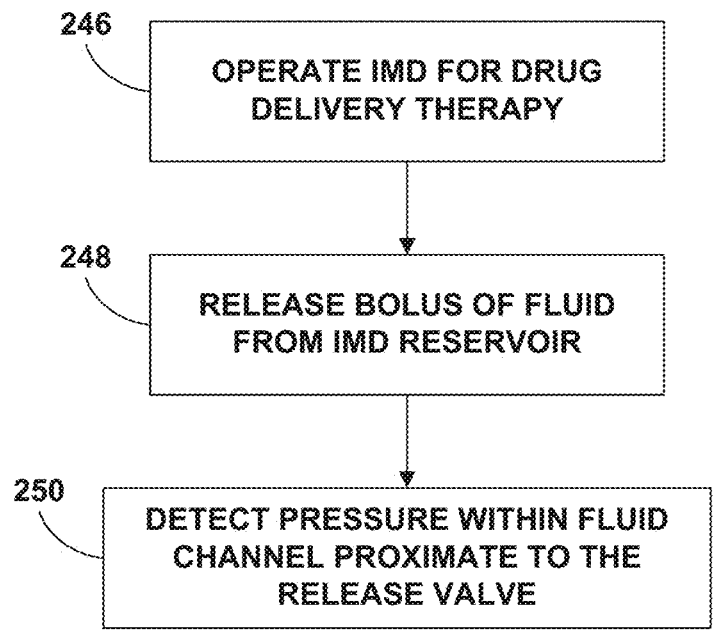
FIG. 17 is a flow diagram illustrating one example of a method for detecting a change in fluid quantity within a pressure sensor consistent with this disclosure.

FIG. 17 is a flow diagram illustrating an example method for detecting a change in fluid quantify with pressure sensor 112. IMD 16 is initially set to operate for drug delivery (246). Drug delivery includes the delivery of fluid from IMD 16 as determined by an automated program or as requested by patient 12. Once IMD 16 is to deliver fluid, IMD 16 releases a bolus, or dose, of fluid from reservoir 122 that defines the reservoir of drug (248). In other examples, IMD 16 may release fluid at a controlled rate over an extended period of time instead of a bolus or dose of fluid at one time. Usually, medical pump 38 expels the requested amount of fluid.

Upon the release of fluid bolus, pressure sensor 112 detects the resulting pressure within reservoir 122 proximate to the release valve 118 (250). The pressure may be indicative of the quantity and/or flow rate of fluid delivered to patient 12. This information may be used to confirm the identified amount and rate of fluid that medical pump 38 was expected to deliver to patient 12. IMD 16 may then store, process, communicate, or otherwise use the output of pressure sensor 112.

In some examples, differences between the detected pressure changes and requested medical pump 38 actions may elicit an alert to programmer 20. Any differences may indicate that medical pump 38 is malfunctioning, there is a clog in catheter 18, or there is some other problem with IMD 16. In other examples, pressure sensor 112 may be used in closed-loop feedback control of medical pump 38. Alternatively, pressure sensor 112 may be used to monitor the refilling of fluid into IMD 16. Above-threshold indications of pressure may be important to limiting damage to IMD 16 or the direct delivery of drug into patient 12 tissues.

The disclosure describes a device that may be capable of providing many features. For example, the pressure sensor itself forms part of the fluid enclosure to prevent intermediary structures between the fluid and the pressure sensor. This modular construction can increase pressure sensor performance while reducing manufacturing time and costs. Also, the fluid enclosure may be constructed with a uniform corrosion resistant and/or biocompatible fluid contact surface to limit fluid to surface interactions that may cause corrosion or other problems. The pressure sensor may also include a conductive diaphragm directly welded to the housing to eliminate adhesives or other less robust attaching mechanisms from being used. The pressure sensor may also provide a capacitive plate that is directly adhered to a supporting rigid insulator without adhesives or bonding materials. As an additional example, the pressure sensor may include a feedthrough pin that is recessed from the capacitive plane of the metal coating on the insulator to eliminate and/or reduce a possibility of undesirable short circuits between two capacitive plates of the pressure sensor.

The disclosure may also provide further features. For example, at least one protrusion may be defined within a housing ferrule to create a gap between the housing ferrule and a support structure of a capacitive plate and provide an attachment structure between these two components. This gap may allow the support structure to be tilted or oriented such that the capacitive plate can be mounted in a desired plane. This protrusion may be part of the housing ferrule or the support structure. As another example, an assembly tool may include a stage of a predetermined height to set one capacitive plate at a desired position and plane within the housing ferrule. In this manner, discrepancies caused by manufacturing inconsistencies with respect to the capacitive plate, insulator, and supporting structure with respect to a desired position for the capacitive plate may be reduced or eliminated.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that may benefit from the subject matter of this disclosure.

Many examples of the disclosure have been described. Various modifications may be made without departing from the scope of the claims. These and other examples are within the scope of the following claims.

The invention claimed is:

1. An implantable medical device (IMD) comprising:
a housing;
one or more electrical components within the housing;
a fluid enclosure wall within the housing and partially defining a fluid enclosure and defining an opening, wherein the fluid enclosure is configured to accommodate a fluid; and
a pressure sensor within the housing, the pressure sensor comprising an operative surface configured to mate to the fluid enclosure wall, the operative surface occluding the opening to partially define the fluid enclosure and separate the fluid from the one or more electrical components, wherein the one or more electrical components are configured to detect, based on a signal from the pressure sensor, a beyond threshold fluid pressure during refill of the IMD with the fluid.

2. The IMD of claim 1, wherein the beyond threshold fluid pressure is indicative of at least one of IMD damage or overflow of the fluid out of the housing.

3. The IMD of claim 1, further comprising a memory configured to store a threshold fluid pressure value, wherein the one or more electrical components are configured to detect the beyond threshold fluid pressure by comparing a fluid pressure represented by the signal from the pressure sensor to the threshold fluid pressure value stored in memory.

4. The IMD of claim 1, wherein the operative surface of the pressure sensor is configured to monitor a pressure of a refill port of the IMD.

5. The IMD of claim 1, wherein the operative surface of the pressure sensor is configured to partially define the fluid enclosure at a position adjacent to a refill port of the IMD.

6. The IMD of claim 1, wherein the operative surface of the pressure sensor is configured to partially define the fluid enclosure, the fluid enclosure defining part of a fluid channel between a refill port of the IMD and a reservoir of the IMD configured to store the fluid.

7. The IMD of claim 1, wherein the fluid enclosure is configured to create a reservoir to store the fluid.

8. The IMD of claim 1, further comprising a telemetry circuit configured to transmit data from the IMD to an external device.

9. The IMD of claim 8, wherein the one or more electrical components comprise processing circuitry configured to control, in response to detecting the beyond threshold fluid pressure, the telemetry circuit to transmit the data to the external device, wherein the data is representative of an alert indicative of the beyond threshold fluid pressure.

10. The IMD of claim 1, wherein the pressure sensor is sized and shaped to self-align in a predetermined rotational orientation to the opening defined by the fluid enclosure wall.

11. The IMD of claim 1, wherein:
the pressure sensor includes a capacitive pressure sensor;
the operative surface comprises a diaphragm mounted to a sensor housing, the diaphragm configured as a first capacitive plate of the capacitive pressure sensor and configured to deflect in response to a pressure of the fluid; and
the pressure sensor comprises a metal film configured as a second capacitive plate of the capacitive pressure sensor.

12. The IMD of claim 1, further comprising the fluid, wherein the fluid comprises a therapeutic agent.

13. A method comprising:
controlling a pump of an implantable medical device (IMD) to deliver a fluid out of the IMD, wherein the IMD comprises:
a housing;
one or more electrical components within the housing;
a fluid enclosure wall within the housing and partially defining a fluid enclosure and defining an opening, wherein the fluid enclosure is configured to accommodate the fluid; and
a pressure sensor within the housing, the pressure sensor comprising an operative surface configured to mate to the fluid enclosure wall, the operative surface occluding the opening to partially define the fluid enclosure and separate the fluid from the one or more electrical components; and detecting, with the one or more electrical components and based on a signal from the pressure sensor, a beyond threshold fluid pressure during refill of the IMD with the fluid.

14. The method of claim 13, wherein the beyond threshold fluid pressure is indicative of at least one of IMD damage or overflow of the fluid out of the housing.

15. The method of claim 13, wherein the beyond threshold fluid pressure is indicative of a blockage located in a catheter connected to the IMD.

16. The method of claim 13, wherein determining the beyond threshold fluid pressure comprises determining the beyond threshold fluid pressure using the operative surface of the pressure sensor, wherein the operative surface monitors a pressure of a refill port of the IMD.

17. The method of claim 13, wherein determining the beyond threshold fluid pressure comprises determining the beyond threshold fluid pressure using the operative surface of the pressure sensor, wherein the operative surface partially defines the fluid enclosure at a position adjacent to a refill port of the IMD.

18. The method of claim 13, wherein determining the beyond threshold fluid pressure comprises determining the beyond threshold fluid pressure using the operative surface of the pressure sensor, wherein the operative surface partially defines the fluid enclosure that is part of a fluid channel between a refill port of the IMD and a reservoir of the IMD configured to store the fluid.

19. The method of claim 13, wherein determining the beyond threshold fluid pressure comprises determining the beyond threshold fluid pressure using the operative surface of the pressure sensor, wherein the operative surface partially defines the fluid enclosure that creates a reservoir configured to store the fluid.

20. The method of claim 13, further comprising controlling a telemetry circuit of the IMD to transmit, to an external device, data representative of an alert indicative of the beyond threshold fluid pressure.

21. The method of claim 20, further comprising presenting, via a user interface of the external device, the alert indicative of the beyond threshold fluid pressure to a user, wherein the user interface is configured to provide the alert as at least one of a visual alert or an audible alert.

22. The method of claim 13, wherein the fluid comprises a therapeutic agent.

23. A system comprising:
an implantable medical device (IMD) configured to connect with a catheter and deliver fluid to a patient via the catheter, wherein the IMD comprises:
 a housing;
 one or more electrical components within the housing;
 a fluid enclosure wall within the housing and partially defining a fluid enclosure and defining an opening, wherein the fluid enclosure is configured to accommodate the fluid;
 a pressure sensor within the housing, the pressure sensor comprising an operative surface configured to mate to the fluid enclosure wall, the operative surface occluding the opening to partially define the fluid enclosure and separate the fluid from the one or more electrical components, wherein the one or more electrical components are configured to detect, based on a signal from the pressure sensor, a beyond threshold fluid pressure during refill of the IMD with the fluid; and
 telemetry circuitry configured to transmit data representative of the beyond threshold fluid pressure; and
an external device comprising a user interface, wherein the external device is configured to:
 receive, from the IMD, the data representative of the beyond threshold fluid pressure; and
 present, via the user interface, an alert indicative of the beyond threshold fluid pressure.

24. The system of claim 23, wherein the beyond threshold fluid pressure is indicative of at least one of IMD damage or overflow of the fluid out of the IMD.

25. The system of claim 23, wherein the operative surface of the pressure sensor is configured to partially define the fluid enclosure, and wherein the operative surface monitors a pressure of a refill port of the IMD.

26. The system of claim 23, wherein the operative surface of the pressure sensor is configured to partially define the fluid enclosure, the fluid enclosure being part of a fluid channel between a refill port of the IMD and a reservoir of the IMD configured to store the fluid.

27. The system of claim 23, wherein the fluid enclosure is configured to create a reservoir to store the fluid.

* * * * *